US011690691B2

(12) United States Patent
Yakimovich et al.

(10) Patent No.: US 11,690,691 B2
(45) Date of Patent: Jul. 4, 2023

(54) SYSTEM AND APPARATUS FOR CRUSH PREVENTION FOR MEDICAL ROBOT APPLICATIONS

(71) Applicant: Covidien LP, Mansfield, MA (US)

(72) Inventors: Terris Yakimovich, Munich (DE); Ruben Baerenweiler, Markdorf (DE)

(73) Assignee: Covidien LP, Mansfield, MA (US)

( * ) Notice: Subject to any disclaimer, the term of this patent is extended or adjusted under 35 U.S.C. 154(b) by 905 days.

(21) Appl. No.: 16/486,204

(22) PCT Filed: Feb. 14, 2018

(86) PCT No.: PCT/US2018/018088
§ 371 (c)(1),
(2) Date: Aug. 15, 2019

(87) PCT Pub. No.: WO2018/152141
PCT Pub. Date: Aug. 23, 2018

(65) Prior Publication Data
US 2020/0000536 A1 Jan. 2, 2020

Related U.S. Application Data

(60) Provisional application No. 62/459,318, filed on Feb. 15, 2017.

(51) Int. Cl.
*A61B 90/00* (2016.01)
*B25J 13/08* (2006.01)
(Continued)

(52) U.S. Cl.
CPC .............. *A61B 34/37* (2016.02); *B25J 13/085* (2013.01); *B25J 18/04* (2013.01); *B25J 19/02* (2013.01); *A61B 2090/065* (2016.02)

(58) Field of Classification Search
CPC .............. A61B 34/37; A61B 2090/065; A61B 2017/00119; A61B 34/30;
(Continued)

(56) References Cited

U.S. PATENT DOCUMENTS 4,591,944 A   5/1986 Gravel
4,691,694 A * 9/1987 Boyd ................. A63B 21/0058
                                                482/901

(Continued)

FOREIGN PATENT DOCUMENTS

CN   101227870 A   7/2008
CN   102525582 A   7/2012
(Continued)

OTHER PUBLICATIONS

Supplementary European Search Report dated Nov. 23, 2020 issued in corresponding EP Appln. No 18754323.6.
(Continued)

*Primary Examiner* — Jaime Figueroa
(74) *Attorney, Agent, or Firm* — Carter, DeLuca & Farrell LLP

(57) ABSTRACT

A surgical robotic arm includes a first link and a second link, wherein at least one of the first link or second link is movable relative to each other. The surgical robotic arm also includes a sensor assembly coupled to at least one of the first link or the second link. The sensor assembly includes a force sensing resistor assembly configured to measure force and an interface member disposed over the force sensing resistor assembly, the interface member configured to engage the at least one force sensing resistor assembly due to the interface member contacting an obstruction.

20 Claims, 37 Drawing Sheets

(51) Int. Cl.
*A61B 34/37* (2016.01)
*B25J 18/04* (2006.01)
*B25J 19/02* (2006.01)

(58) Field of Classification Search
CPC ........... A61B 2017/00123; A61B 2018/00898; A61B 2090/036; B25J 13/085; B25J 18/04; B25J 19/02; B25J 9/1676; B25J 19/06
USPC .............................. 700/245–264; 73/12.01; 318/568.11–568.25
See application file for complete search history.

(56) References Cited

U.S. PATENT DOCUMENTS

| | | | |
|---|---|---|---|
| 5,562,843 A | 10/1996 | Yasumoto | |
| 5,691,898 A * | 11/1997 | Rosenberg | G05G 9/047 345/161 |
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,175,769 B2 * | 5/2012 | Perrin | E05F 15/43 701/45 |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |

(56) References Cited

U.S. PATENT DOCUMENTS

| | | | |
|---|---|---|---|
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,942,828 B1 * | 1/2015 | Schecter ............ A61H 31/004 607/116 |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,310 B2 * | 6/2017 | Nowlin ............... A61B 34/30 |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,827,679 B2 * | 11/2017 | Kuth .................... B25J 9/1676 |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 * | 2/2018 | Blumenkranz ........ A61B 34/71 |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,265,854 B2 * | 4/2019 | Chen .................... A61B 34/30 |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,368,878 B2 * | 8/2019 | Lavallee ............... A61B 34/70 |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |

(56) References Cited

U.S. PATENT DOCUMENTS

| | | | |
|---|---|---|---|
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,786,327 B2* | 9/2020 | Anderson | A61B 90/37 |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,771 B2* | 5/2021 | Srimohanarajah | A61B 90/361 |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 2002/0045888 A1* | 4/2002 | Ramans | A61B 34/71 606/1 |
| 2003/0079549 A1 | 5/2003 | Lokhorst et al. | |
| 2004/0130528 A1 | 7/2004 | Baker et al. | |
| 2005/0093821 A1* | 5/2005 | Massie | G06F 1/206 345/184 |
| 2005/0259069 A1 | 11/2005 | Baker et al. | |
| 2009/0248038 A1 | 10/2009 | Blumenkranz et al. | |
| 2010/0077868 A1 | 4/2010 | Joung | |
| 2013/0168336 A1 | 7/2013 | Kim et al. | |
| 2015/0051733 A1 | 2/2015 | Nowlin et al. | |
| 2016/0113720 A1* | 4/2016 | Lavallee | A61B 17/15 901/9 |
| 2016/0207197 A1 | 7/2016 | Takahashi et al. | |
| 2016/0279796 A1 | 9/2016 | Naitou et al. | |
| 2016/0346935 A1 | 12/2016 | Nakayama et al. | |
| 2016/0361125 A1 | 12/2016 | Balicki et al. | |
| 2018/0036884 A1* | 2/2018 | Chen | A61B 34/30 |
| 2018/0071029 A1* | 3/2018 | Srimohanarajah | A61B 90/37 |
| 2018/0092706 A1* | 4/2018 | Anderson | A61B 34/30 |
| 2020/0253678 A1* | 8/2020 | Hulford | A61B 90/30 |
| 2021/0085424 A1* | 3/2021 | Hulford | A61B 34/25 |

FOREIGN PATENT DOCUMENTS

| | | |
|---|---|---|
| EP | 2280662 A1 | 2/2011 |
| JP | 2001287189 A | 10/2001 |
| JP | 2002254384 A | 9/2002 |
| JP | 2003071778 A | 3/2003 |
| JP | 2004022791 A | 1/2004 |
| JP | 2006250705 A | 9/2006 |
| JP | 2016132080 A | 7/2016 |
| JP | 2017009289 A | 1/2017 |
| WO | 2017015599 A1 | 1/2017 |

OTHER PUBLICATIONS

Japanese Office Action dated Nov. 2, 2021 issued in corresponding JP Appln. No. 2019-541427.

Indian Office Action dated Sep. 24, 2021 issued in corresponding IN Appln. No. 201917025728.

International Search Report dated May 28, 2018 and Written Opinion completed May 28, 2018, corresponding to counterpart Int'l Patent Application PCT/US2018/018088.

Cirillo et al.: "A Proximity/Contact-Force Sensor for Human Safety in Industrial Robot Environment"; ResearchGate; Conference Paper Jul. 2013; <https://www.researchgate.net/publication/261270528> retrieved on Sep. 27, 2016.

Office Action issued in corresponding Chinese application 201880005472.2 dated Apr. 25, 2022, together with English language translation (29 pages).

Japanese Office Action dated Jun. 15, 2022 issued in corresponding JP Appln. No. 2019-541427.

Australian Office Action dated Nov. 2, 2022, issued in corresponding Australian application No. 2018221456, 3 pages.

Australian Examination Report issued in corresponding application AU 2018221456 dated Oct. 5, 2022 (3 pages).

* cited by examiner

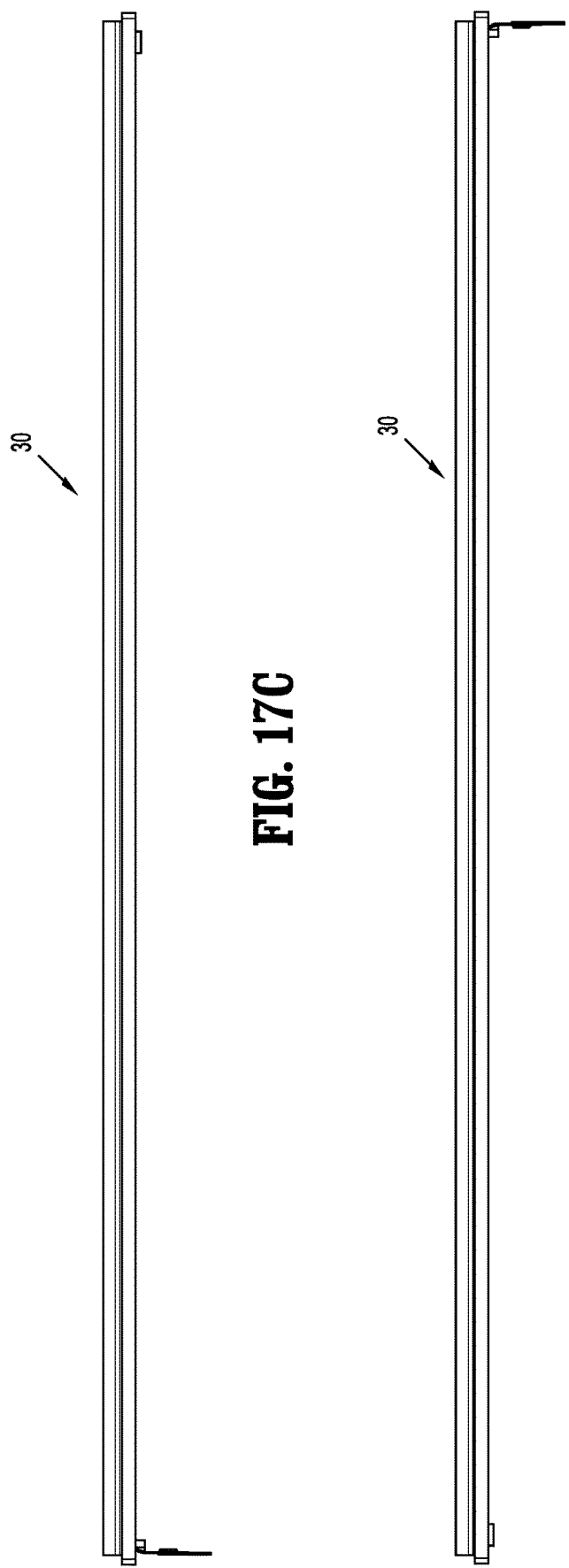

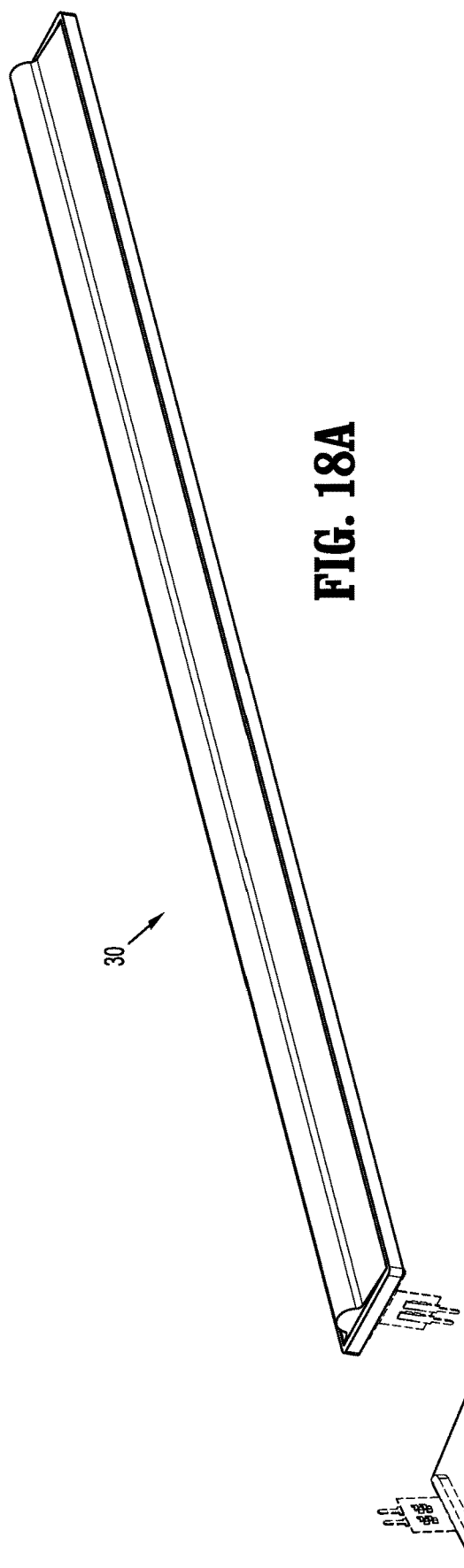
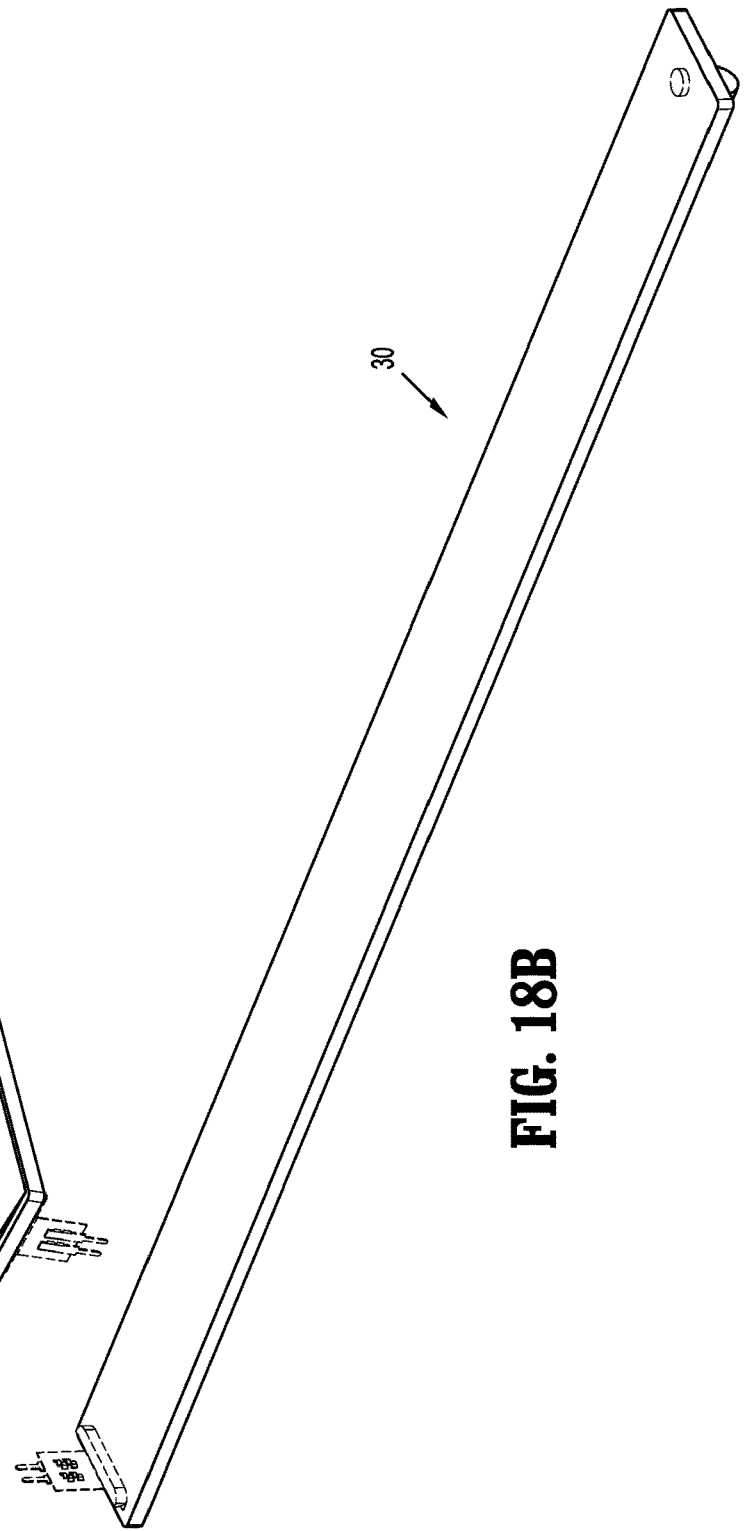
FIG. 18A
FIG. 18B

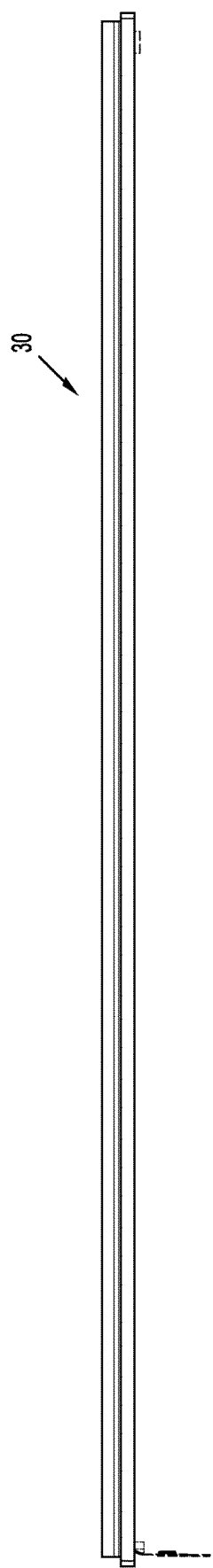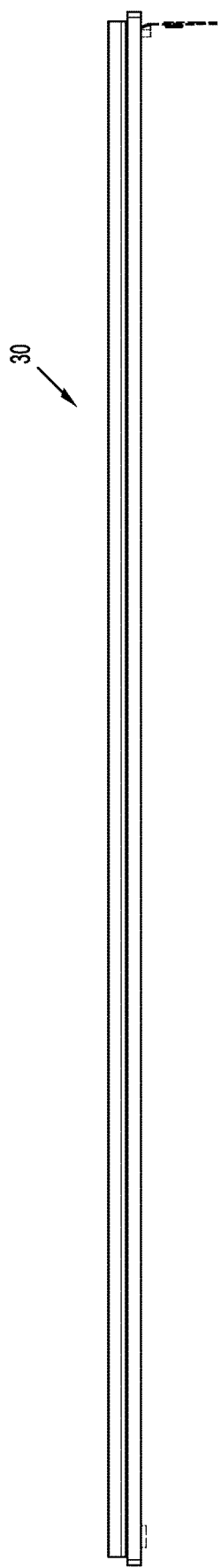
FIG. 18C
FIG. 18D

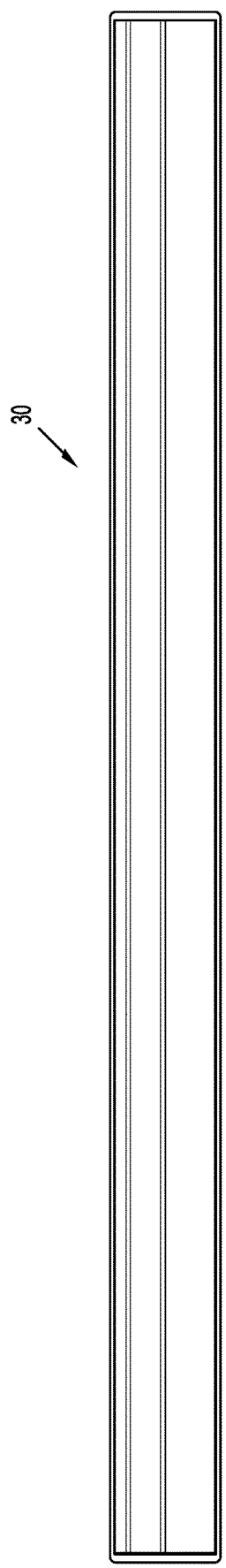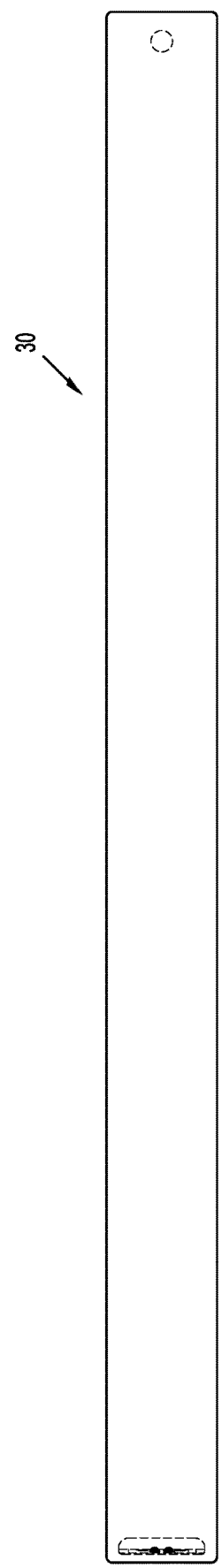
FIG. 18E
FIG. 18F

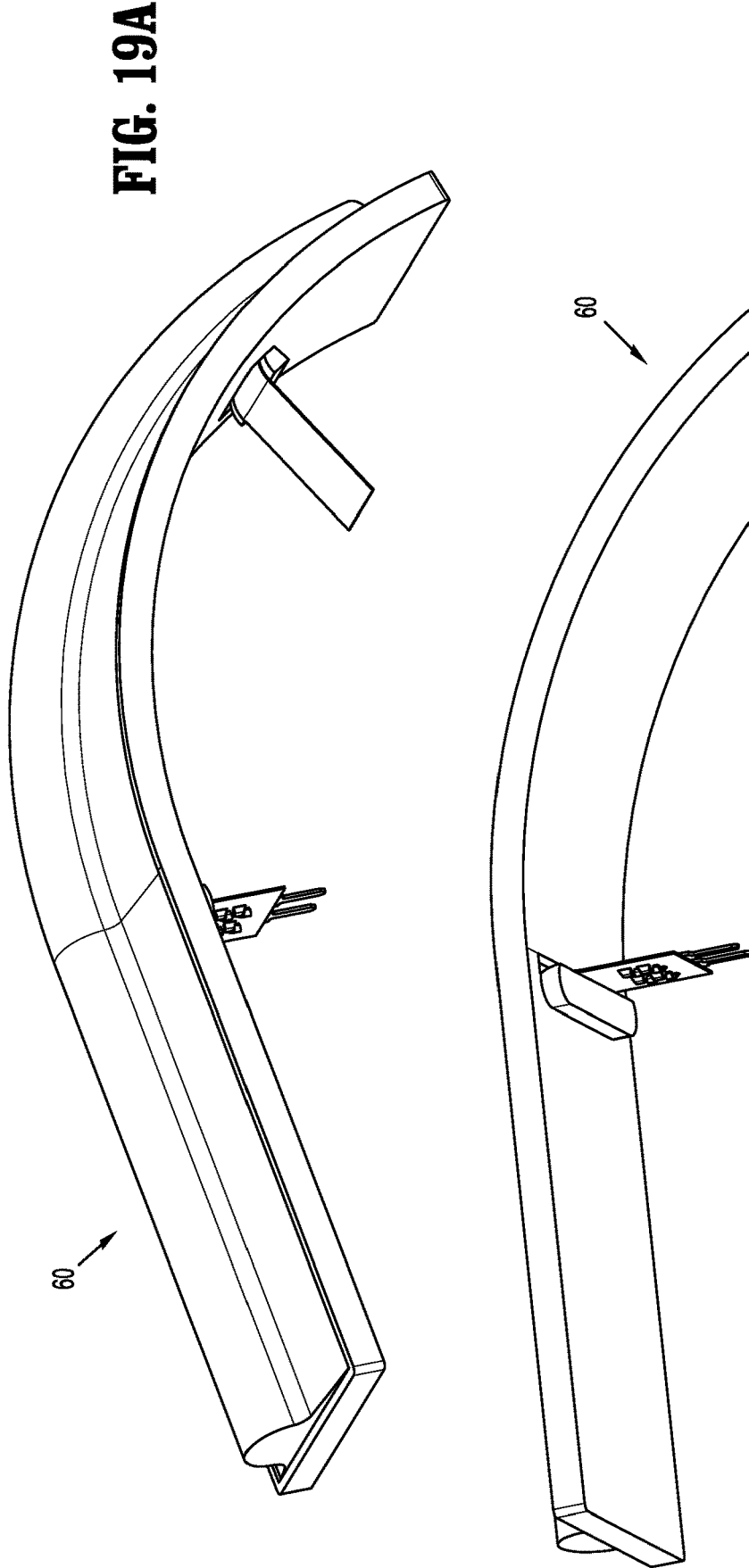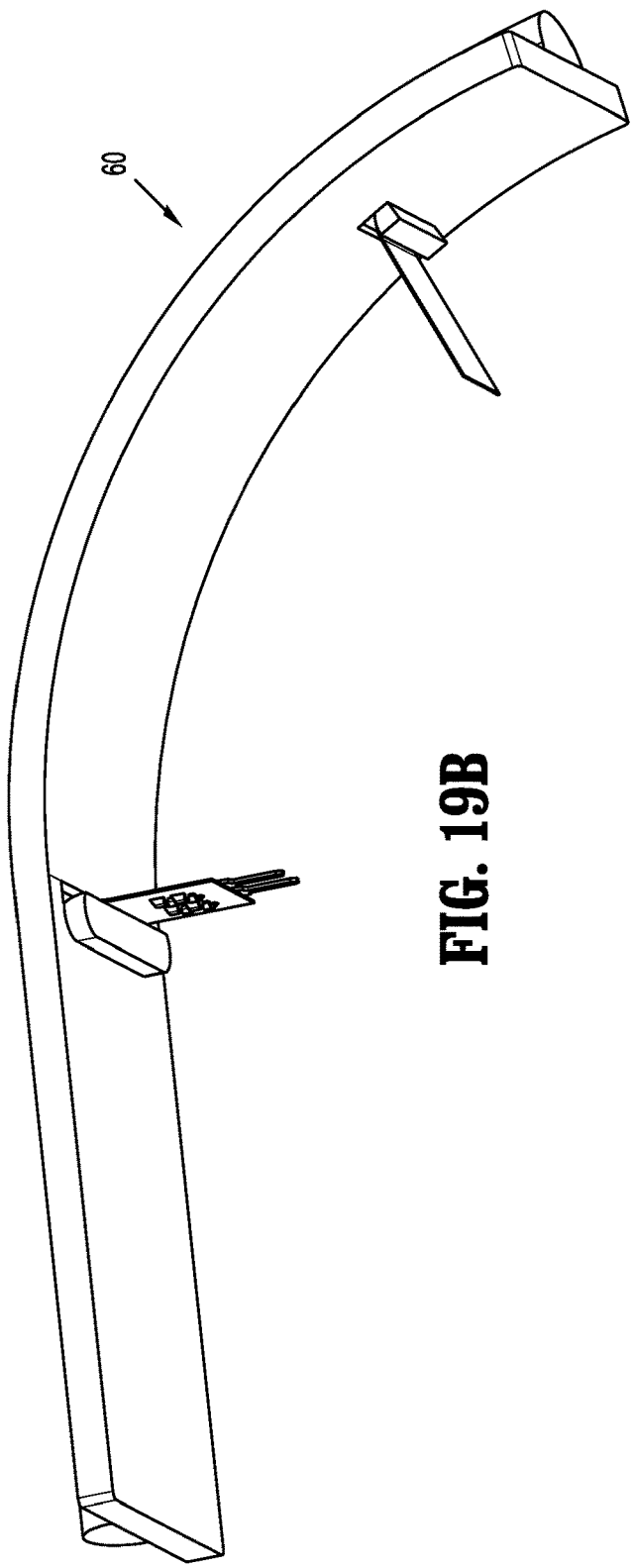

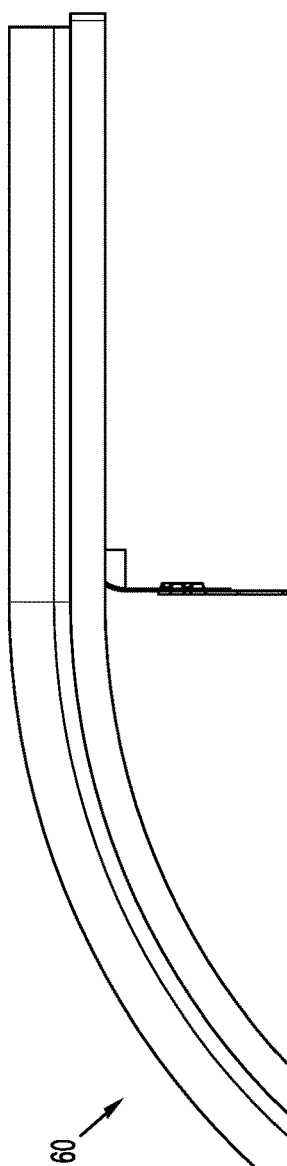
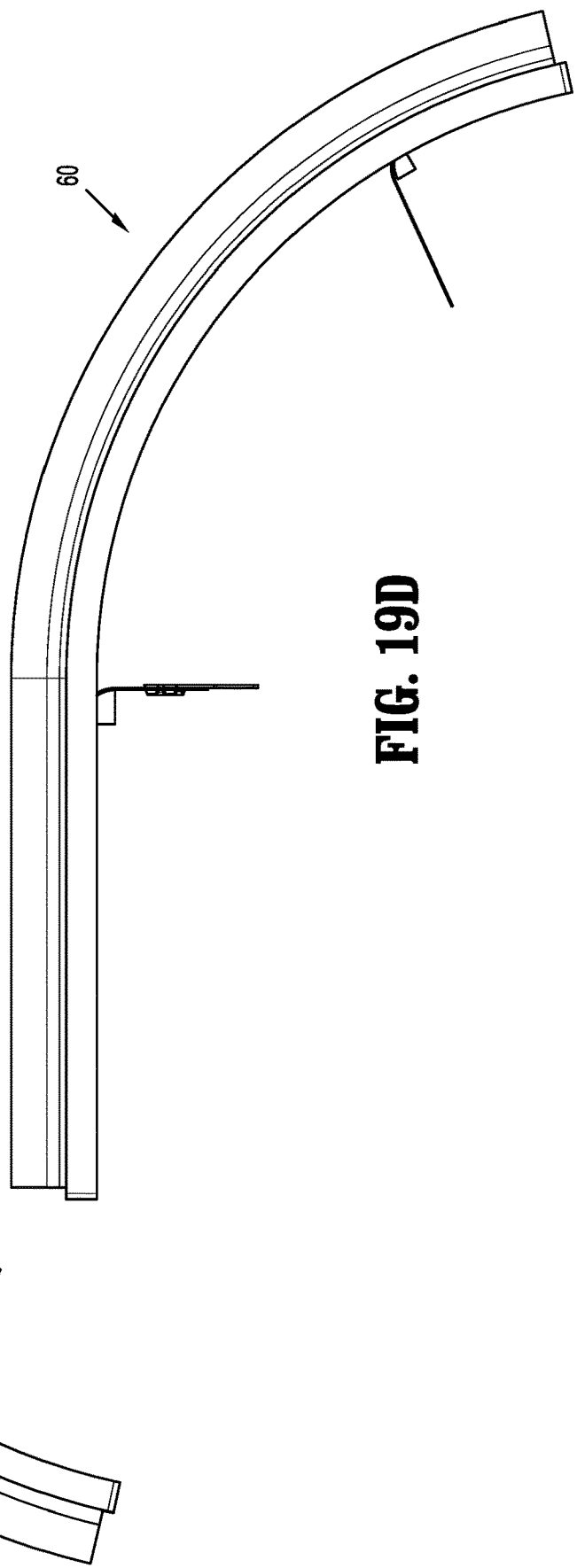
FIG. 19C
FIG. 19D

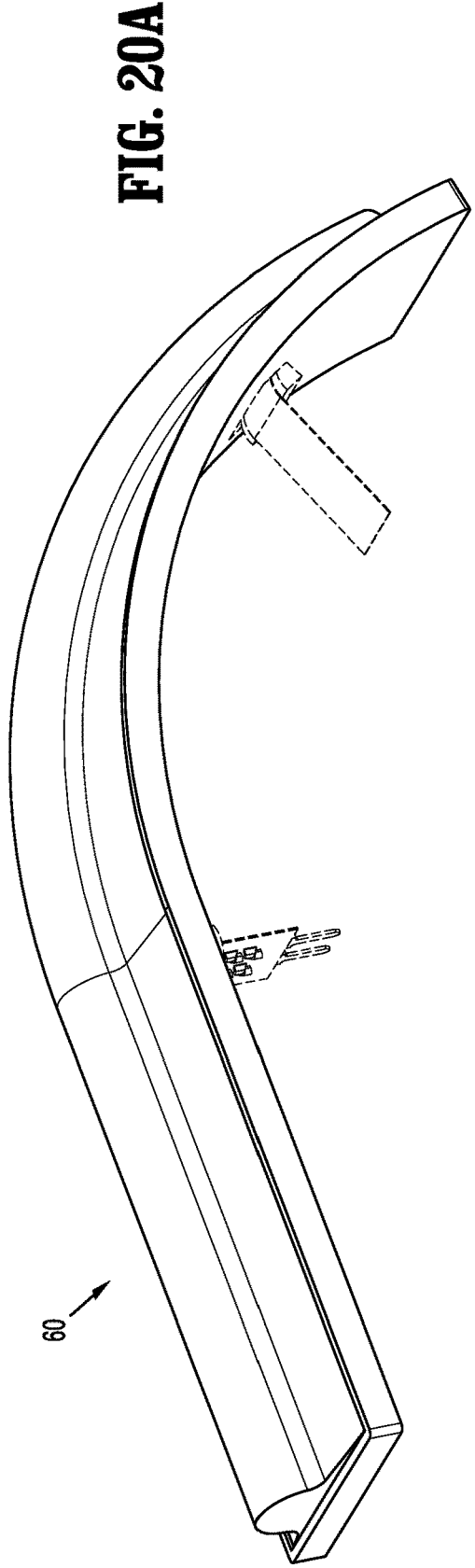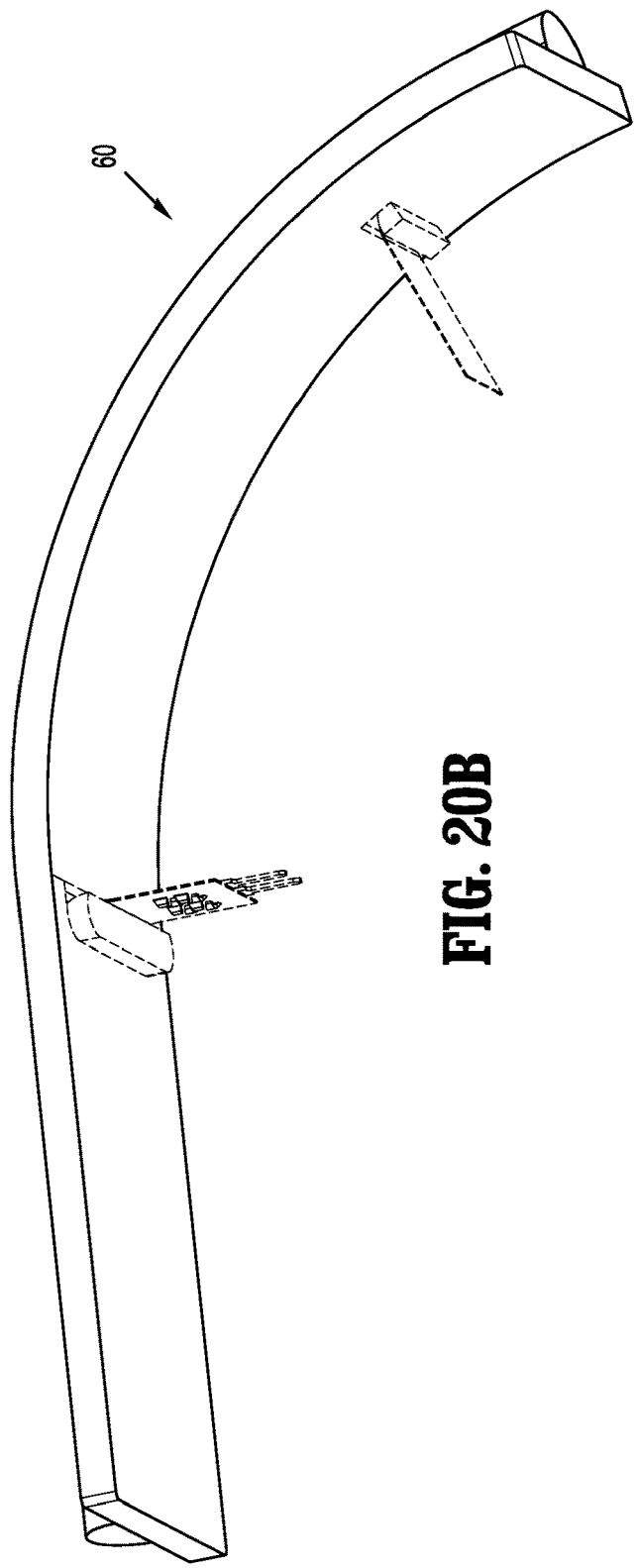

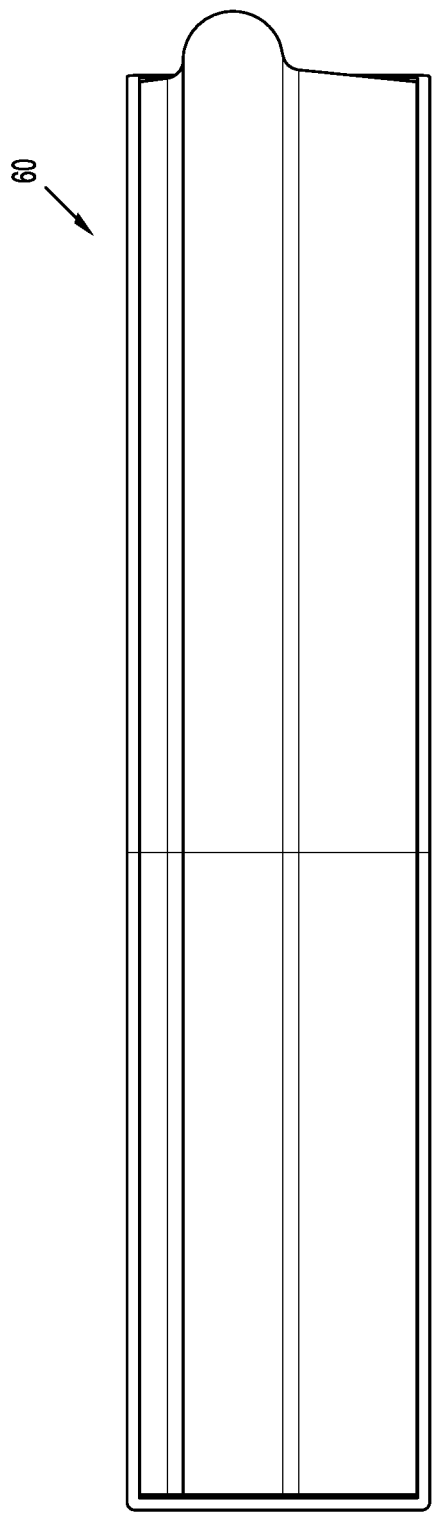
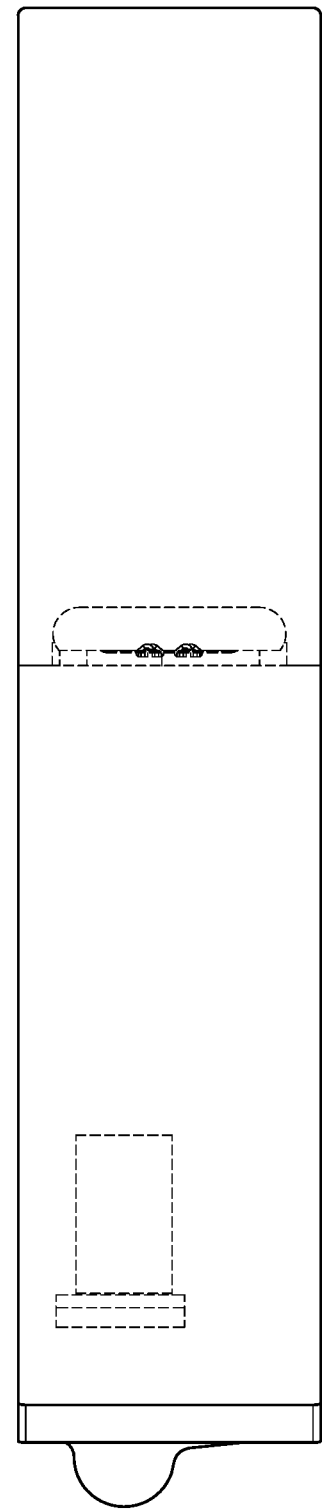
FIG. 20E
FIG. 20F

SYSTEM AND APPARATUS FOR CRUSH PREVENTION FOR MEDICAL ROBOT APPLICATIONS

CROSS-REFERENCE TO RELATED APPLICATIONS

This application is a U.S. National Stage Application filed under 35 U.S.C. § 371(a) of International Patent Application Serial No. PCT/US2018/018088, filed Feb. 14, 2018, which claims the benefit of and priority to U.S. Provisional Patent Application Ser. No. 62/459,318, filed Feb. 15, 2017, the entire disclosure of which is incorporated by reference herein.

BACKGROUND

Surgical robotic systems are currently being used in minimally invasive medical procedures. Some surgical robotic systems may include a console supporting a surgical robotic arm and a surgical instrument having an end effector (e.g., forceps or grasping tool) coupled to the robotic arm, which is actuated by the robotic arm. The robotic arm may include a plurality of links, whose movement and pivoting may pose a shearing and crushing danger to the user's fingers and hands. The presence of a sterile drape between the robotic arm and the user prevents the practical application of many conventional sensors. The present disclosure provides for a sensor system capable of recognizing when obstructions (e.g., hands, fingers, objects, etc.) contact high-risk areas of the robotic arm and reacts preemptively to avoid any injury by posting a warning to the user and immediately stopping motion of the robot, by providing audible and/or tactile feedback, or some other desired reaction.

SUMMARY

The present disclosure provides one or more sensor assemblies disposed on one or more links of a robotic arm to prevent injury to users when coming in contact with moving links of the robotic arm. The sensor assemblies include an elastomeric interface member having a curved or raised rib and a force sensing resistor ("FSR") disposed underneath the interface member. The FSR is configured to detect force. The FSR is coupled to a control device, which is configured to interpret a given level of resistance as force, and correlate the measured force to physical contact of the robotic arm with an obstruction.

According to one embodiment, a surgical robotic arm is disclosed. The surgical robotic arm includes a first link and a second link, wherein at least one of the first link or second link is movable relative to each other. The surgical robotic arm also includes a sensor assembly coupled to at least one of the first link or the second link. The sensor assembly includes: a force sensing resistor assembly configured to measure force and an interface member disposed over the force sensing resistor assembly, the interface member configured to engage the at least one force sensing resistor assembly due to the interface member contacting an obstruction.

According to one aspect of the above embodiment, the interface member includes an outer protrusion and an inner protrusion. The outer protrusion may be offset from a center of the at least one force sensing resistor assembly, specifically, from a longitudinal centerline axis of the at least one force sensing resistor assembly.

According to another aspect of the above embodiment, the sensor assembly is curved and includes a first force sensing resistor assembly disposed at a first end of the sensor assembly and a second force sensing resistor assembly disposed at a second end of the sensor assembly. The interface member may also be curved and includes a rigid bridge configured to engage at least one of the first force sensing resistor assembly or the second force sensing resistor assembly due to the interface member contacting an obstruction.

According to another embodiment of the present disclosure, a surgical robotic system is disclosed. The surgical robotic system includes a surgical robotic arm having a first link and a second link, wherein at least one of the first link or second link is movable relative to each other. The surgical robotic arm also includes a sensor assembly coupled to at least one of the first link or the second link. The sensor assembly includes: a force sensing resistor assembly configured to measure force; and an interface member disposed over the force sensing resistor assembly, the interface member configured to engage the force sensing resistor assembly in response to contacting an obstruction. The surgical robotic system also includes a control device coupled to the surgical robotic arm and the sensor assembly. The control device configured to control movement of the surgical robotic arm based on the force measured by the force sensing resistor assembly.

According to one aspect of any of the above embodiments, the force sensing resistor includes an upper conductive layer and a lower conductive substrate, the upper conductive layer configured to contact the lower conductive substrate in response to engagement with the interface member. An amount of contact between the upper conductive layer and the lower conductive substrate is representative of the force.

According to another aspect of the above embodiment, the control device is configured to determine connectivity of the force sensing resistor to the control device, and/or to detect the presence of broken cables or broken electrical traces or the like. In an embodiment, the sensor assembly may include a known finite resistance at zero-load, and wherein the method may recognize a failure in connectivity (e.g., broken cable, loose connector, broken sensor, etc.). In an embodiment, a resistor, of known resistance, may bridge an upper conductive layer and a lower conductive layer of the sensor assembly, wherein the resistor is located opposite a connector of the sensor assembly.

According to a further aspect of the above embodiment, the control device includes a memory storing a set of instructions and a processor configured to execute the set of instructions.

The memory may store a force threshold. The control device may be configured to: compare the force measured by the force sensing resistor assembly to the force threshold; and control at least one of the first link or second link based on the comparison of the force measured by the force sensing resistor assembly to the force threshold.

According to a further embodiment of the present disclosure, a method for controlling a surgical robotic arm is disclosed. The method includes: moving at least one of a first link or a second link of a surgical robotic arm; measuring a force exerted on a sensor assembly coupled to at least one of the first link or the second link of the surgical robotic arm; determining at a control device whether the force measured by the sensor assembly exceeds a first threshold corresponding to contact with an obstruction; and controlling movement of at least one of the first link or the second link of the surgical robotic arm based on the force measured by the sensor assembly exceeding the first threshold.

According to one aspect of the above embodiment, the method further includes: outputting an alert based on the force measured by the sensor assembly exceeding the first threshold.

According to another aspect of the above embodiment, the method further includes: comparing the force measured by the sensor assembly to a second threshold, which is lower than the first threshold; and outputting an alert based on the force measured by the sensor assembly exceeding the second threshold.

According to a further aspect of the above embodiment, the method further includes: stopping the surgical robotic arm based on the force measured by the sensor assembly exceeding the first threshold.

According to one aspect of the above embodiment, the method further includes: continuously monitoring a signal from the sensor assembly; and verifying connectivity of the sensor assembly based on an interruption of the signal from the sensor assembly. In an embodiment, the sensor assembly may include a known finite resistance at zero-load, and wherein the method may recognize a failure in connectivity (e.g., broken cable, loose connector, broken sensor, etc.). In an embodiment, the method includes providing a resistor, of known resistance, that bridges an upper conductive layer and a lower conductive substrate of the sensor assembly, wherein the resistor is located opposite a connector of the sensor assembly.

According to a further aspect of the above embodiment, the method further includes: measuring the force exerted on the sensor assembly includes contacting an upper conductive layer and a lower conductive substrate of the sensor assembly to the interface member contacting the obstruction.

According to another embodiment of the present disclosure, a surgical robotic system is disclosed. The system includes a surgical robotic arm having a first link and a second link, wherein at least one of the first link or second link is movable relative to each other; and a sensor assembly coupled to at least one of the first link or the second link, the sensor assembly configured to sense physical contact. The system also includes a cart having: a base; a support mount attached to the base and configured to couple to the surgical robotic arm; a plurality of wheels coupled to the base; and at least one lighting element configured to indicate a status of the surgical robotic arm including the sensor assembly sensing physical contact.

BRIEF DESCRIPTION OF THE DRAWINGS

Embodiments of the present disclosure are described herein with reference to the accompanying drawings, wherein:

FIG. 17C is a right-side, elevation view of the sensor assembly of FIG. 17A;

FIG. 17D is a left-side, elevation view of the sensor assembly of FIG. 17A;

FIG. 18A is a top, perspective view of the sensor assembly of FIGS. 17A-17H, with portions thereof in phantom;

FIG. 18B is a bottom, perspective view of the sensor assembly of FIG. 18A;

FIG. 18C is a right-side, elevation view of the sensor assembly of FIG. 18A;

FIG. 18D is a left-side, elevation view of the sensor assembly of FIG. 18A;

FIG. 18E is a top, plan view of the sensor assembly of FIG. 18A;

FIG. 18F is a bottom, plan view of the sensor assembly of FIG. 18A;

FIG. 19A is a top, perspective view of a sensor assembly according to an alternate embodiment of the present disclosure;

FIG. 19B is a bottom, perspective view of the sensor assembly of FIG. 19A;

FIG. 19C is a right-side, elevation view of the sensor assembly of FIG. 19A;

FIG. 19D is a left-side, elevation view of the sensor assembly of FIG. 19A;

FIG. 20A is a top, perspective view of the sensor assembly of FIGS. 19A-19H, with portions thereof in phantom;

FIG. 20B is a bottom, perspective view of the sensor assembly of FIG. 20A;

FIG. 20E is a top, plan view of the sensor assembly of FIG. 20A;

FIG. 20F is a bottom, plan view of the sensor assembly of FIG. 20A;

DETAILED DESCRIPTION

Figure 1:
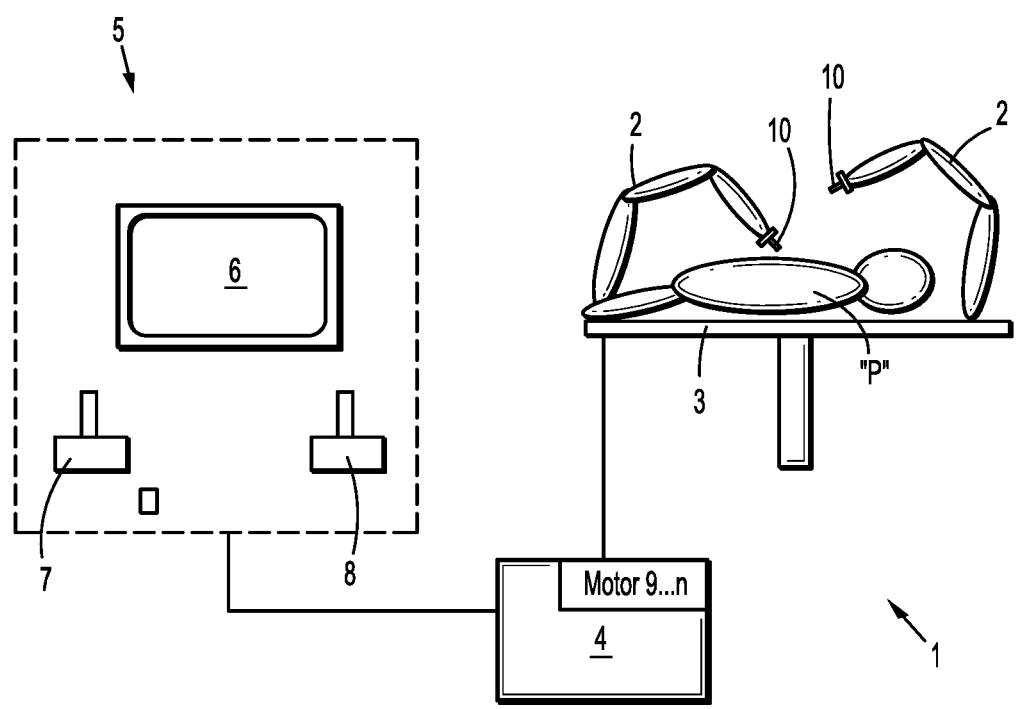
FIG. 1 is a schematic illustration of a surgical robotic system including a surgical robotic arm according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

As will be described in detail below, the present disclosure is directed to a surgical robotic system, which includes a robotic arm having a sensor assembly configured to sense force. The sensor assembly may be disposed on curved or straight portions of the robotic arm. The sensor assembly may be disposed in high injury risk zones on the links of the robotic arm, in particular, portions of links that may pinch or otherwise injure user's appendages or other body parts that may be trapped and crushed by the moving links of the robotic arm. The sensor assembly includes a force sensing resistor ("FSR"), and an elastomeric interface member disposed over the FSR. The surgical robotic system also includes a control device coupled to the FSR. The control device is configured to interpret a given level of resistance of the FSR as force, and correlate the measured force with the amount of physical contact of the robotic arm with a user. Thus, the control device is configured to recognize whether the robotic arm has contacted any obstructions. In embodiments, the sensitivity of the sensors can be adjusted, such that only force above a certain threshold is selected to be indicative of contact with the user or other obstructions. In response to detecting contact with the user, the control device may be configured to preemptively stop any movement of the robotic arm and/or the links where the contact was sensed and output a warning.

Referring initially to FIG. 1, a surgical robotic system 1 includes a plurality of surgical robotic arms 2, each having a surgical instrument 10 removably attached thereto; a control device 4; and an operating console 5 coupled to control device 4. Surgical robotic system 1 is configured for use on a patient "P" lying on a surgical table 3 to be treated in a minimally invasive manner using the surgical instrument 10.

Operating console 5 includes a display device 6, which displays the surgical site and manual input devices 7, 8, by which a clinician is able to remotely control robotic arms 2. Each of the robotic arms 2 may be composed of a plurality of links, which are connected through joints. Robotic arms 2 may be driven by electric drives (not shown) that are connected to control device 4. Control device 4 (e.g., a computer, a logic controller, etc.) is configured to activate the drives, based on a set of programmable instructions stored in memory, in such a way that robotic arms 2 and surgical instruments 10 execute a desired movement according to a movement in response to input from manual input devices 7, 8.

The control device 4 may include a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Control device 4 may control a plurality of motors (e.g., motor 9 . . . n), each of which is configured to actuate the surgical instrument 10 to effect operation and/or movement of surgical instrument 10. It is contemplated that control device 4 coordinates the activation of the various motors (motor 9 . . . n) to coordinate a clockwise or counter-clockwise rotation of drive members (not shown) to coordinate operation and/or movement of the surgical instrument 10. In embodiments, each motor of the plurality of motors (motor 9 . . . n) can be configured to actuate a drive rod, cable, or a lever arm (not shown) to effect operation and/or movement of each surgical instrument 10.

For a detailed discussion of the construction and operation of a surgical robotic system, reference may be made to U.S. Pat. No. 8,828,023, filed on Nov. 3, 2011, entitled "Medical Workstation," the entire contents of which are incorporated by reference herein.

Figure 2:
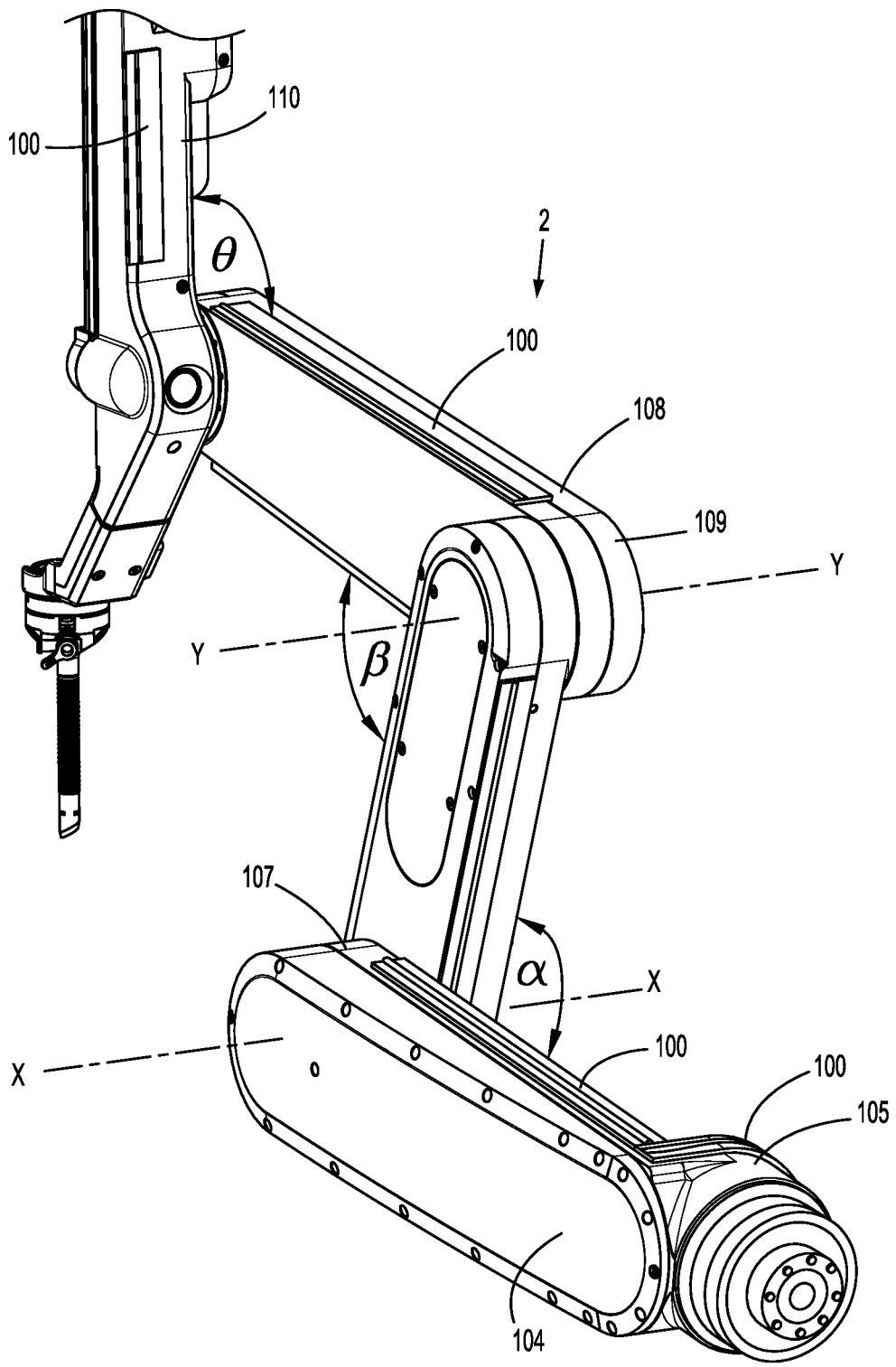
FIG. 2 is a perspective view of a surgical robotic arm of the surgical robotic system of FIG. 1 according to the present disclosure.
Figure 3:
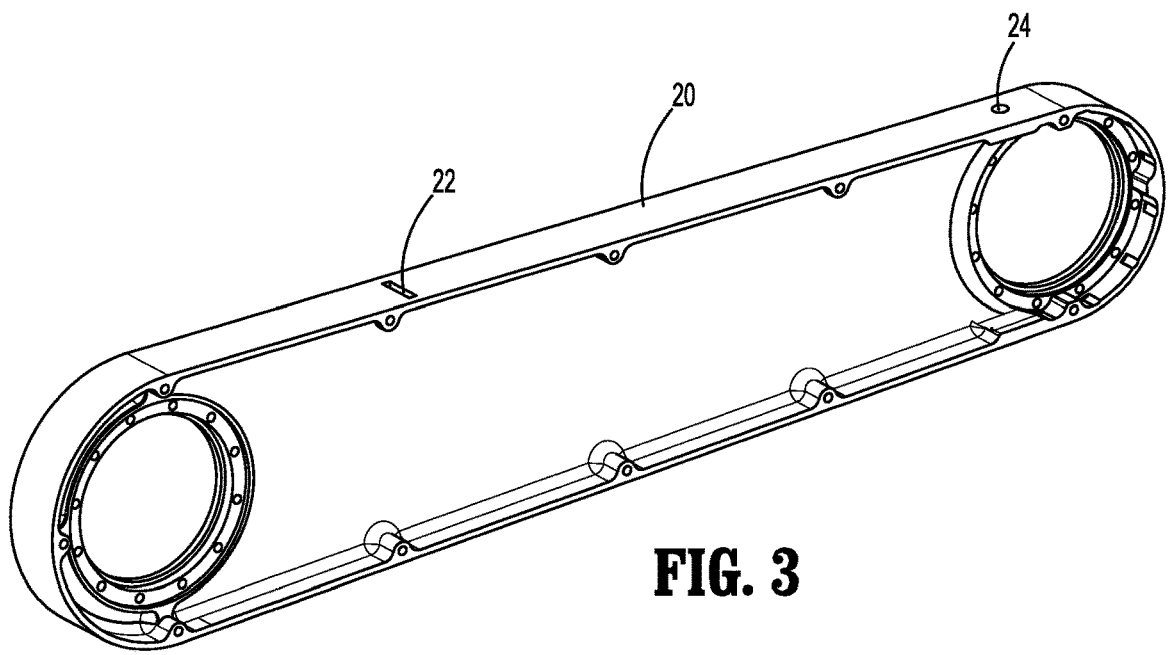
FIG. 3 is a perspective view of a housing portion of a link of the surgical robotic arm of FIG. 2.

With reference to FIGS. 2 and 3, the robotic arm 2 includes a plurality of movable links, a first link 104, a second link 106, a third link 108, and a holder 110, which are coupled to each other by actuators (not shown) allowing for movement of the robotic arm 2 into various configurations. The holder 110 is configured to receive an instrument drive unit which is configured to couple to an actuation mechanism of the surgical instrument 10. Instrument drive unit transfers actuation forces from its motors to the surgical instrument 10 to actuate components (e.g., end effectors) of the surgical instrument 10.

The first link 104 includes a curved base 105 configured to secure the robotic arm 2 to a movable base, such as movable cart or stand (not shown) or to a stationary base, such as the table 3. The second link 106 is rotatable at a joint 107 and about an axis "X-X" relative to the first link 104, such that an angle α defined by the first and second links 104 and 106 is from about 0° to about 140°. The third link 108 is rotatable at a joint 109 and about an axis "Y-Y" relative to the second link 106, such that an angle β defined by the second and third links 106 and 108 is from about 0° to about 140°. The holder 110 is rotatable relative to the third link 108 such that an angle θ defined by the holder 110 and the third link 108 is from about 25° to about 160°. Since the edges of the movable links of the robotic arm 2, namely, the first and second links 104 and 106, the second and third links 106 and 108, etc., are capable of being flush with each other, there is a possibility of trapping and crushing various obstructions, such as user's appendages, fingers, etc., between the links 104, 106, and 108 as well as the holder 110 of the robotic arm 2.

The present disclosure provides for a sensor system configured to detect physical contact between the movable links of the robotic arm 2 and to control the robotic arm 2. The robotic arm 2 may include one or more sensor assemblies 100 disposed on any link (e.g., the links 104, 106, and 108 and the holder 110) of the robotic arm 2. The sensor assemblies 100 may be disposed on any surface that present a high risk of crushing, shearing, or otherwise injuring body parts that may be caught by the robotic arm 2 during its movement. In embodiments, the sensor assemblies 100 may be disposed adjacent an inner edge (e.g., an edge that is closest to a neighboring link) of the first, second, and third links 104, 106, and 108, such as sensor assembly 30 of FIGS. 4-8 or sensor assembly 53 of FIGS. 10 and 11. In addition, the sensor assemblies 100 may also be disposed on an outer edge of the holder 110, which may contact the first link 104 when all of the first, second, and third links 104, 106, and 108 are collapsed along with the holder 110. In further embodiments, the sensor assembly 100 may be disposed on a curved surface of the curved base 105 of the first link 104, such as curved sensor assembly 60 of FIGS. 10-11 to prevent the joint 109 crushing user's appendages resting on the curved base 105.

Figure 4:
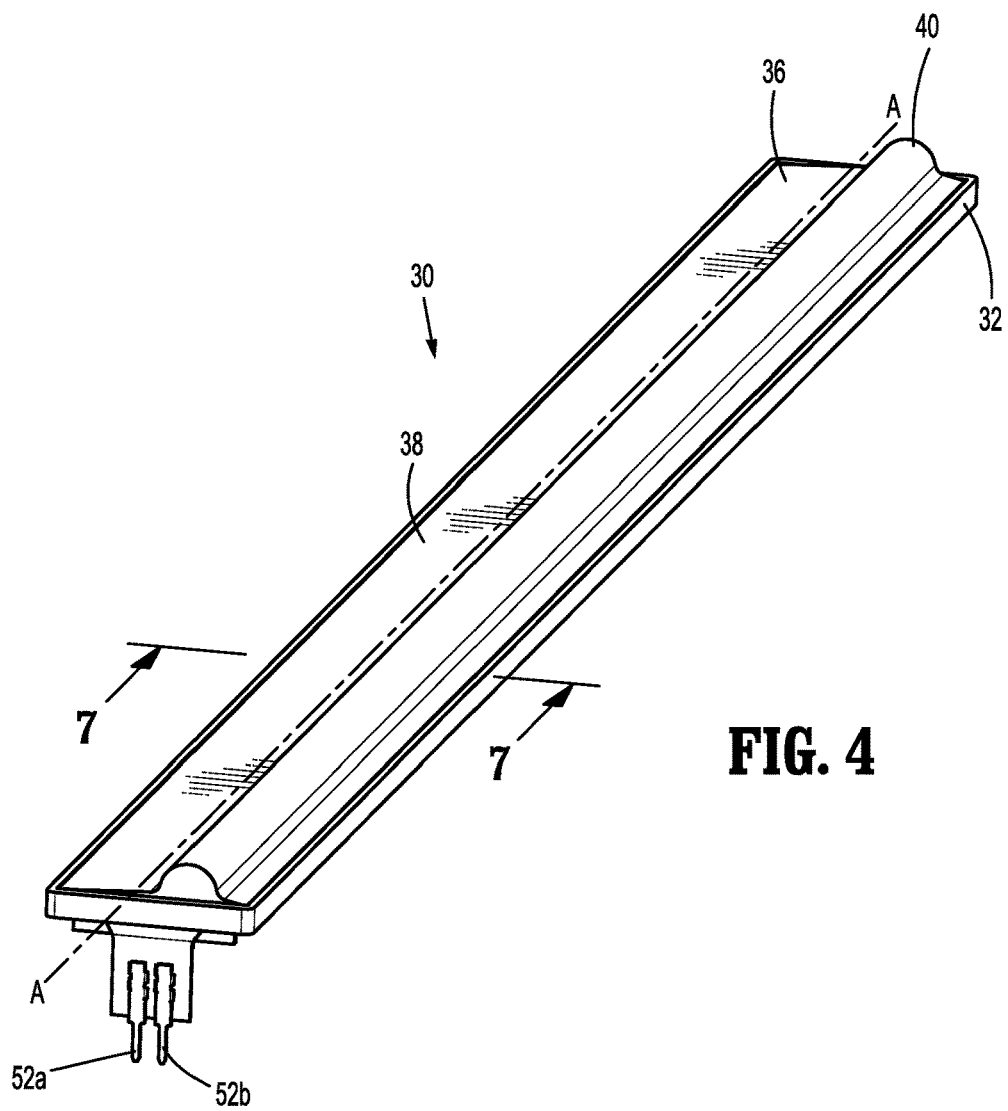
FIG. 4 is a top, perspective view of a sensor assembly disposed on surgical robotic arm of FIG. 1 according to one embodiment the present disclosure.
Figure 5:
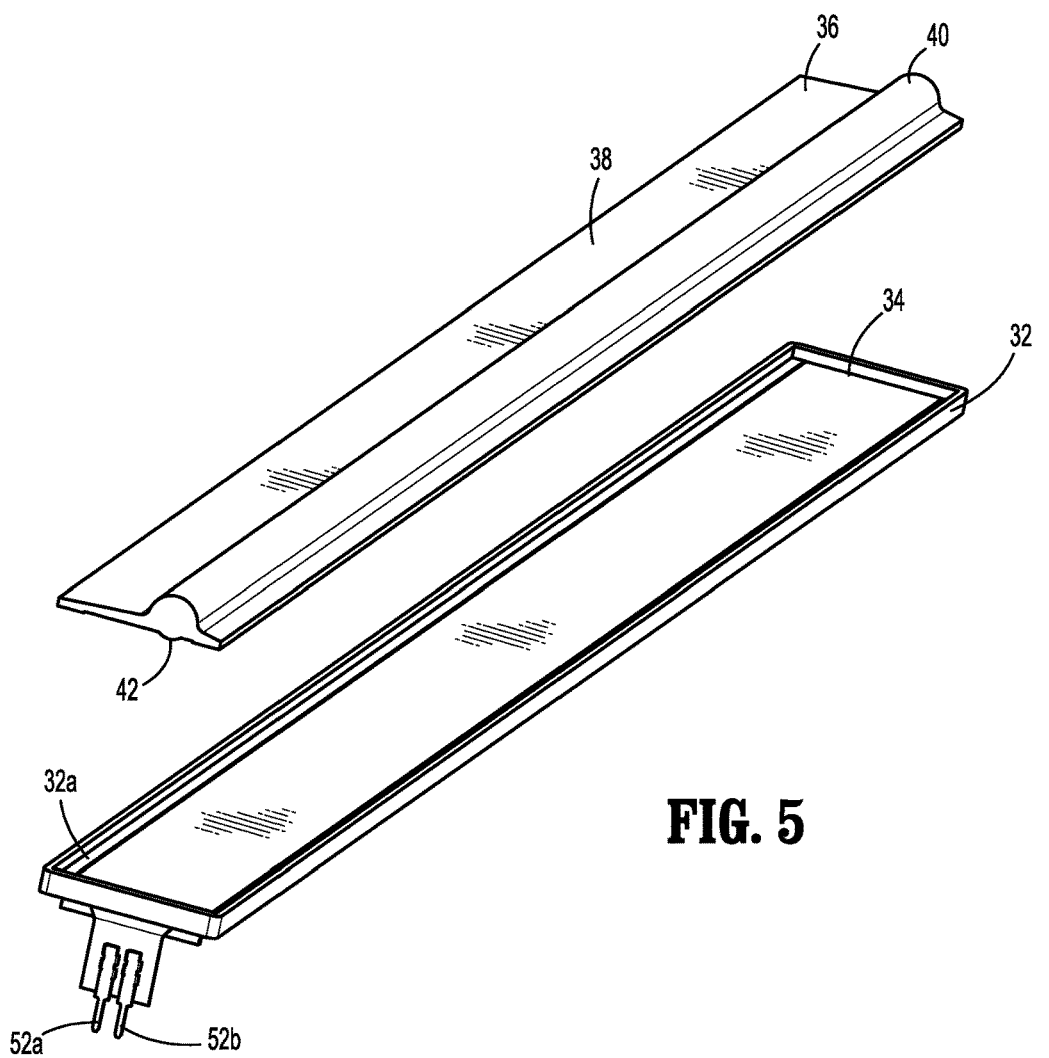
FIG. 5 is a perspective view of the sensor assembly of FIG. 4 with parts separated.
Figure 6:
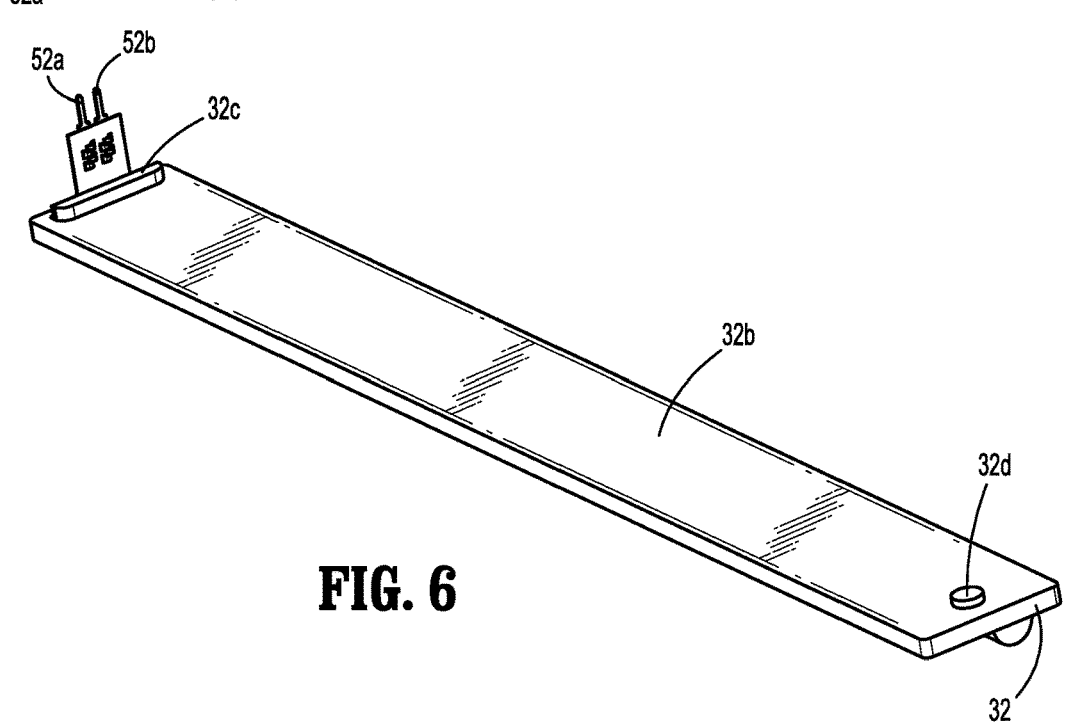
FIG. 6 is a bottom, perspective view of the sensor assembly of FIG. 4.

With reference to FIGS. 4-8, the sensor assembly 30 includes a base housing 32, having a force sensing resistor assembly 34 (FIGS. 6 and 7) disposed within the base housing 32, and an interface member 36 disposed over the force sensing resistor assembly 34. As shown in FIGS. 5 and 6, the base housing 32 includes an inner surface 32a, an outer surface 32b, and a pair of projections 32c and 32d disposed on the inner surface 32b. The force sensing resistor assembly 34 may be secured to the inner surface 32a of the base housing 32 using an adhesive or any other suitable methods.

With reference to FIG. 3, a housing portion 20 of one of the first, second, or third links 104, 106, or 108 is shown. The housing portion 20 includes a slit 22 and an opening 24, which are configured to receive and engage the projections 32c and 32d (FIG. 5), respectively, which are disposed on the outer surface 32b, thereby aligning and securing the base housing 32 to the housing portion 20 of one of the first, second, or third links 104, 106, or 108.

Figure 7:
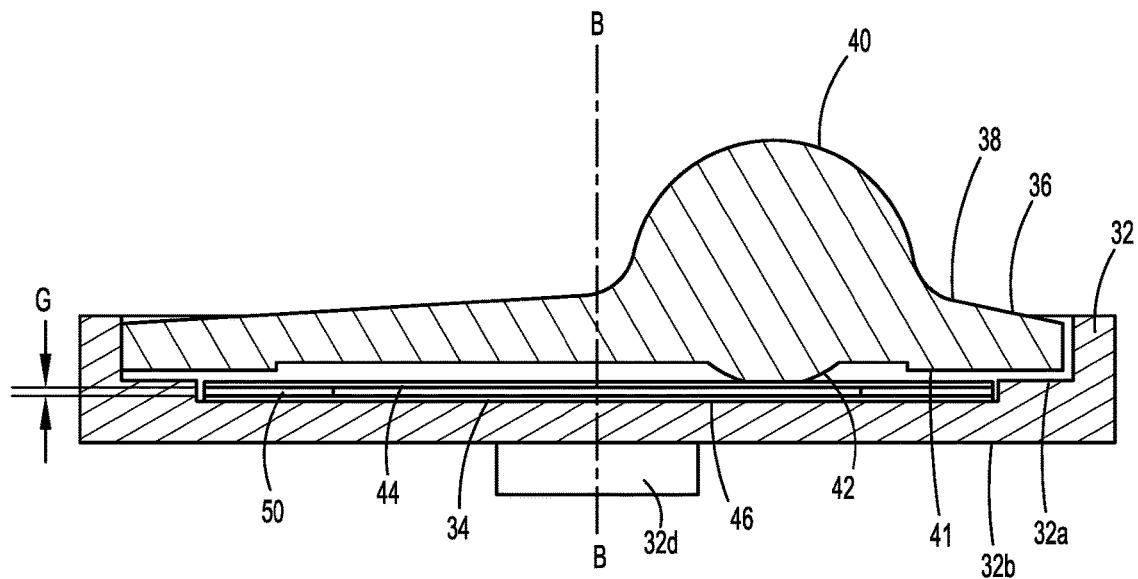
FIG. 7 is a side, cross-sectional view of the sensor assembly of FIG. 4 taken through line "7-7" of FIG. 4.

With reference to FIGS. 5 and 7, the interface member 36 includes an outer surface 38 having an outer protuberance 40 and an inner surface 41 having an inner protuberance 42. In embodiments, the interface member 36 may overlay only a portion of the force sensing resistor assembly 34. The outer and inner protuberances 40 and 42 extend along a longitudinal axis "A-A" (FIG. 3) defined by the sensor assembly 30. In embodiments, the outer and inner protuberances 40 and 42 may extend along only a portion of the length of the interface member 36. The outer and inner protuberances 40 and 42 may have any suitable cross-section, including, but not limited to, curved, polygonal, or combinations thereof. The interface member 36 may be formed from any suitable elastomeric material, such as natural or synthetic rubber including polyurethane, polyisoprene, polybutadiene, chloroprene, polyisobutylene, as well as combinations and copolymers thereof.

The inner protuberance 42 extends from the inner surface 41 of the interface member 36 and is configured to contact the force sensing resistor assembly 34, without compressing it unless the interface member 36 is compressed. The outer and inner protuberances 40 and 42 may be offset from a center line "B-B" (FIG. 7) of the force sensing resistor assembly 34. In this configuration, the side of outer protuberance 40 is disposed closer to the edge of the first, second or third links 104, 106, or 108 of the robotic arm 2 as shown in FIG. 2.

In embodiments, the force sensing resistor assembly 34 may be coupled directly to one of the first, second, or third links 104, 106, or 108, using adhesive or any suitable methods, thereby obviating the need for the base housing 32. In further embodiments, the interface member 36 may include a compartment therein to enclose the force sensing resistor assembly 34. The interface member 36 may then be secured to one of the first, second, or third links 104, 106, or 108.

The force sensing resistor assembly 34 includes an upper conductive layer 44 and a lower conductive substrate 46. The upper conductive layer 44 and the lower conductive substrate 46 may be formed from flexible polymer sheets including any suitable polymer, such as polyethylene terephthalate, polyimide, polycarbonate, etc. The inside surface of the upper conductive layer 44 may be coated with a conductive ink, such as a carbon-based ink. In embodiments, the upper conductive layer 44 may also be formed from a flexible conductive sheet, such as a deformable metal sheet.

Figure 8:
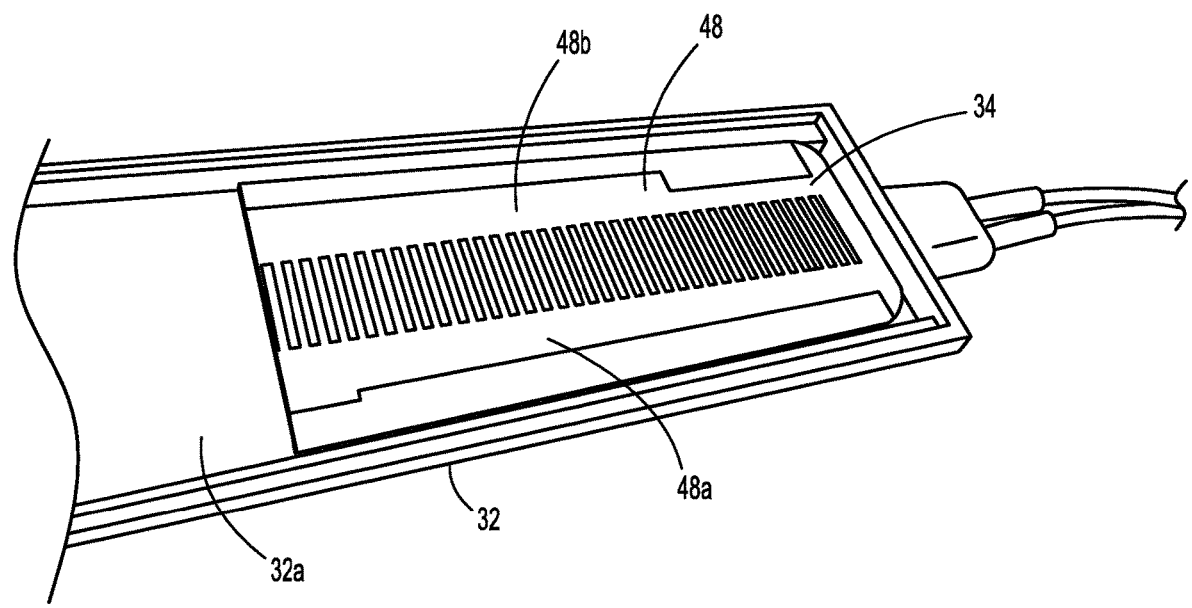
FIG. 8 is a perspective view of the sensor assembly of FIG. 4 without an interface member.

As shown in FIG. 8, the lower conductive substrate 46 may be a printed flexible circuit board including an interdigitated circuit 48 having a first electrode pattern 48a and a second electrode pattern 48b, such that a plurality of finger electrodes of each of the electrode patterns 48a and 48b interlock with each other. The electrode patterns 48a and 48b may be screen printed from silver polymer thick film ink or any other conductive material. In embodiments, the electrode patterns 48a and 48b may be formed out of gold plated copper or other conductive metals.

With reference to FIG. 7, the upper conductive layer 44 and the lower conductive substrate 46 are separated by a spacer 50 disposed therebetween. The spacer 50 is disposed around the perimeter of each of the upper conductive layer 44 and the lower conductive substrate 46 and may be attached to each of them using an adhesive, thus maintaining a gap "G" therebetween. Thus, the spacer 50 separates the upper conductive layer 44 and the lower conductive substrate 46 and secures them together. In embodiments, the spacer 50 may be screen printed using a pressure sensitive adhesive or, alternatively, may be cut from a film pressure sensitive adhesive. In further embodiments, the spacer 50 may be built up (e.g., 3D printed) using any combination of materials that can both separate and adhere to the upper conductive layer 44 and the lower conductive substrate 46.

During operation, the force sensing resistor assembly 34 senses force when the upper conductive layer 44 contacts the lower conductive substrate 46. Thus, the force sensing resistor assembly 34 is in an open circuit until the force sensing resistor assembly 34 is activated by the interface member 36. When the upper conductive layer 44 contacts the lower conductive substrate 46, the upper conductive layer 44 shorts across the interdigitated fingers of the electrode patterns 48a and 48b of the lower conductive substrate 46, transitioning from an open circuit to a short circuit. As the interface member 36 encounters an obstruction or is otherwise actuated by an external force (e.g., due to contact by a hand or appendage of clinician), the inner protuberance 42 of the interface member 36 presses down on the upper conductive layer 44, which in turn, contacts the lower conductive substrate 46. The amount of sensed force is based on the amount of surface area of the upper conductive layer 44 contacting the lower conductive substrate 46. In particular, the applied force changes the resistance of the force sensing resistor assembly 34 based on the amount of electrical contact between the electrode patterns 48a and 48b. The lower conductive substrate 46 may be formed from a graphite-based, pressure sensitive material that increases in electrical conductivity (reduced electrical resistance) proportional to the amount of pressure applied. The resistance is inversely proportional to the applied force and is then used by the control device 4 to determine the force.

With reference to FIGS. 4-6, the force sensing resistor assembly 34 also includes a pair of contacts 52a and 52b extending through the base housing 32. The contacts 52a and 52b are coupled to the electrode patterns 48a and 48b, respectively, and provide a voltage signal representative of resistance between the electrode patterns 48a and 48b to the control device 4, which then determines the amount of force exerted on the force sensing resistor assembly 34. The force sensing resistor assembly 34 has a minimum actuation threshold, namely, an initial force at which the force sensing resistor assembly 34 transitions from an open circuit to a short circuit.

Figure 9A:
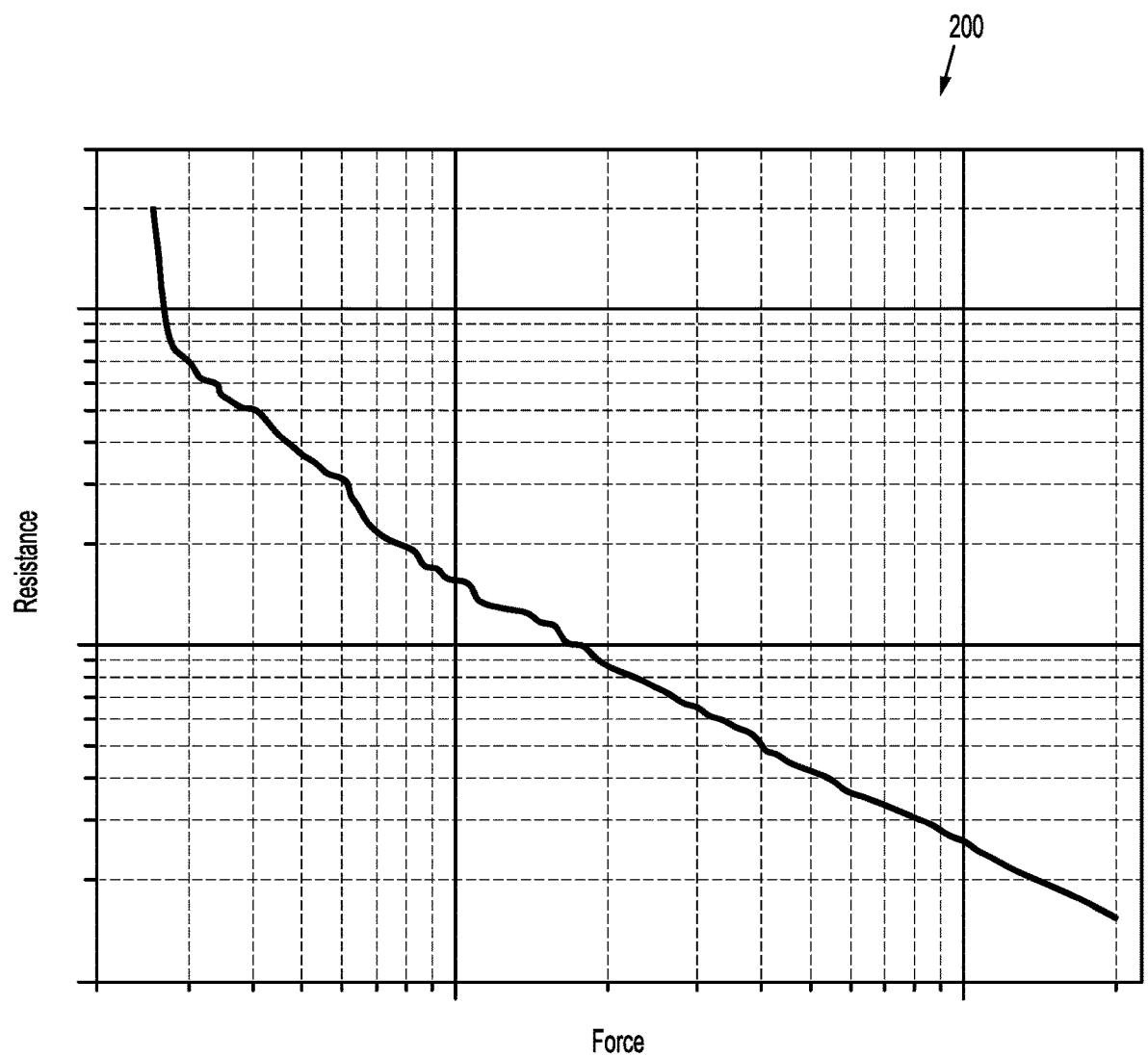
FIG. 9A is a plot of resistance as a function of force using a logarithmic scale illustrating a response range of the sensor assembly of FIG. 4.

FIG. 9A is a plot 200 illustrating a relationship between resistance and force using a logarithmic scale. The plot 200 illustrates the operational range of the force sensing resistor assembly 34, which may be, for illustrative purposes, from about 1,000 gram force ("gf") to about 10,000 gf corresponding to about 100,000 kilo ohms ("kΩ") of resistance to about 1,000 kΩ, respectively. The measurable force range depends on the thickness of the substrate and overlay, flexibility of the upper conductive layer 44 and the lower conductive substrate 46, size and shape of the interface member 36, and thickness of the spacer 50, etc. As shown in plot 200, after activation of the force sensing resistor assembly 34, 64, or 65, the resistance decreases very rapidly, at slightly higher and then intermediate forces, the resistance follows an inverse power law, and at the high forces, the response eventually saturates to a point where increases in force yield little or no decrease in resistance.

Figure 9B:
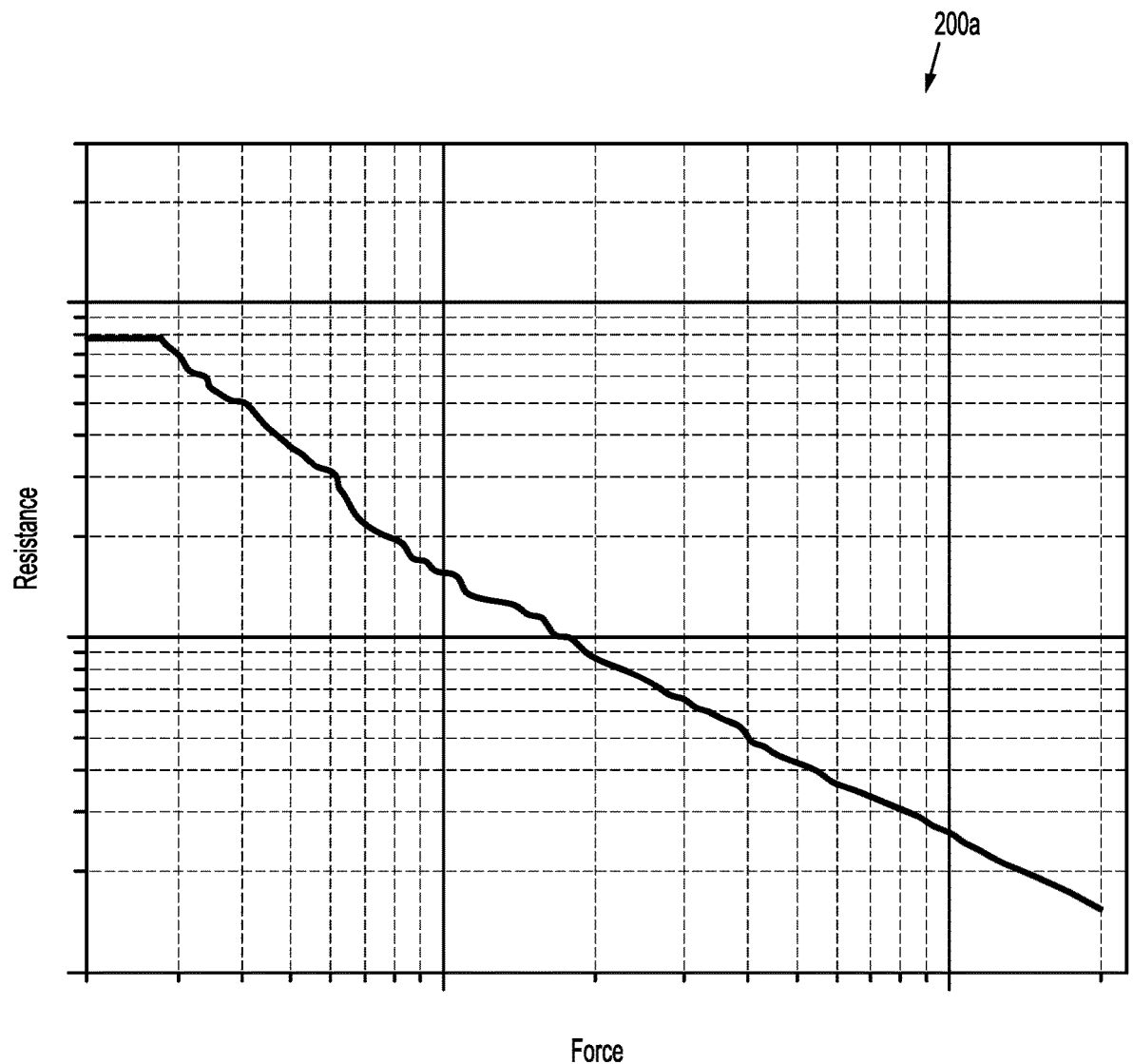
FIG. 9B is a further plot of resistance as a function of force using a logarithmic scale illustrating a response range of the sensor assembly of FIG. 4.

As illustrated in FIG. 9, the resistance approaches infinity as the force approaches zero. With reference to FIG. 9B, a plot 200a is provided illustrating a relationship between resistance and force using a logarithmic scale, wherein the resistance approaches a finite value as the force approaches zero.

Figure 11:
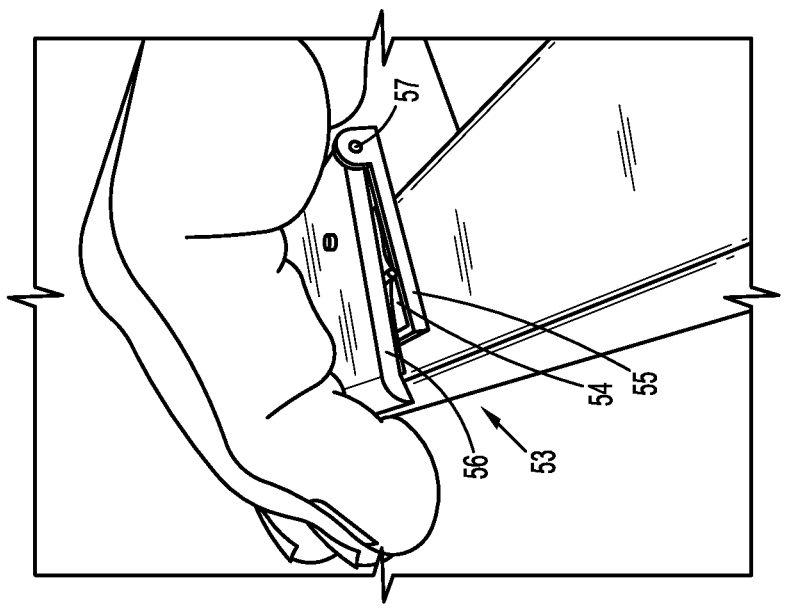
FIG. 11 is a perspective view of the sensor assembly of FIG. 10 with the interface member in a closed configuration.
Figure 10:
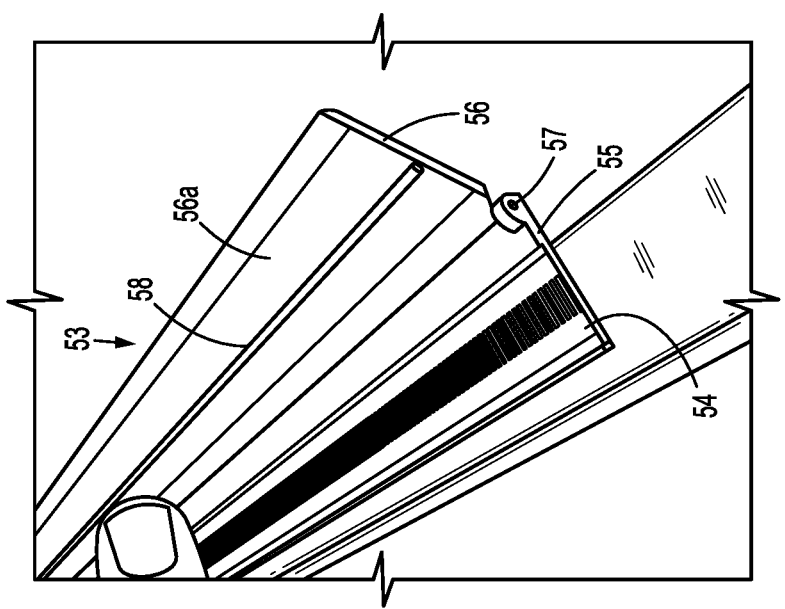
FIG. 10 is a perspective view of a sensor assembly, with an interface member in an open configuration, according to another embodiment of the present disclosure.

With reference to FIGS. 10 and 11, another embodiment of a sensor assembly 53, which is substantially similar to the sensor assembly 30, includes a base housing 55 having a force sensing resistor assembly 54. The sensor assembly 53 also includes an interface member 56 that is coupled to the base housing 55 via a hinge 57.

The interface member 56 includes an inner surface 56a having an inner protuberance 58. As shown in FIG. 10, the inner protuberance 58 extends along a longitudinal axis "C-C" defined by the sensor assembly 30. The inner protuberance 58 may have any suitable cross-section, including, but not limited to, curved, polygonal, or combinations thereof. The inner protuberance 58 may also be a series of discreet protuberances and not a continuous rib. As shown in FIG. 11, the interface member 56 rests over the force sensing resistor assembly 54, until the interface member 56 is sufficiently engaged to press the inner protuberance 58 on the force sensing resistor assembly 54. The sensor assembly 53 operates in the same manner as the sensor assembly 30 described above. In an embodiment, interface member 56 may be rigid, with protuberance 58 being elastic, to inhibit damage to force sensing resistor assembly 54. In an embodiment, rigid interface member 56 can be made up of a series of discreet rigid shells running the length of the sensitized region rather than just one long rigid interface member 56. In an embodiment, the hinged pivoting of rigid interface member 56 may be biased with a spring to hold rigid interface member 56 to force sensing resistor assembly 54, such that any slack is removed between protuberance 58 and force sensing resistor assembly 54. In an embodiment, rigid interface member 56 may extend beyond the corner edge of the robot link 20 (e.g., cantilever) in order to "sensitize" an edge region thereof. In an embodiment rigid interface member 56 may not be hinged but held down against force sensing resistor assembly 54 via biasing elements (e.g., resilient foam) running along at least both sides of force sensing resistor assembly 54.

Figure 12:
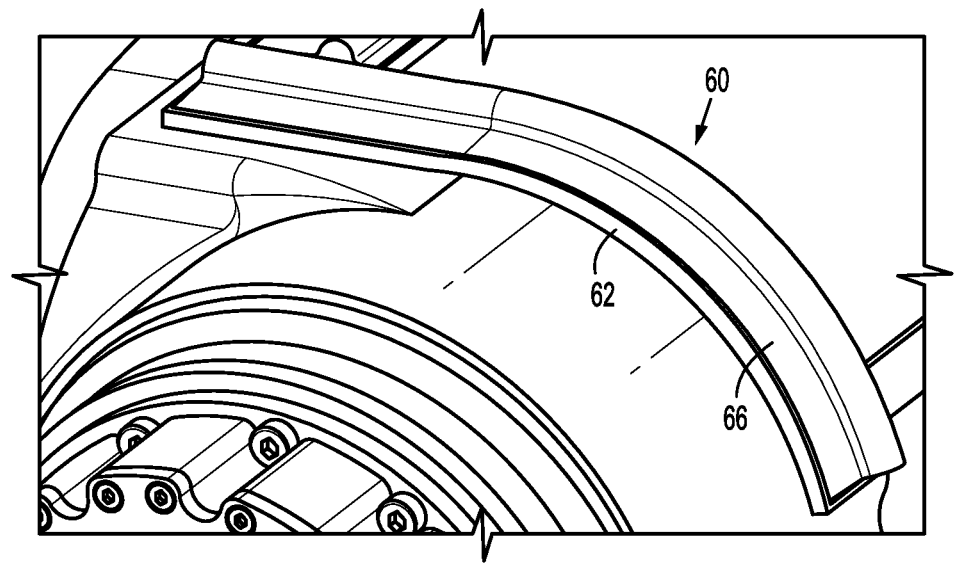
FIG. 12 is a perspective view of a sensor assembly according to a further embodiment.
Figure 13:
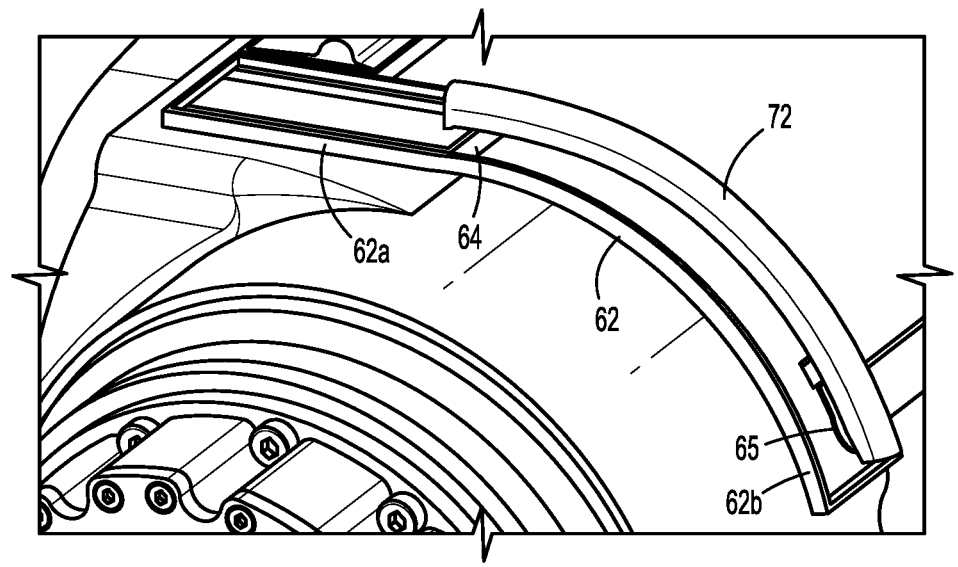
FIG. 13 is a perspective view of the sensor assembly of FIG. 12 without an interface member.
Figure 14:
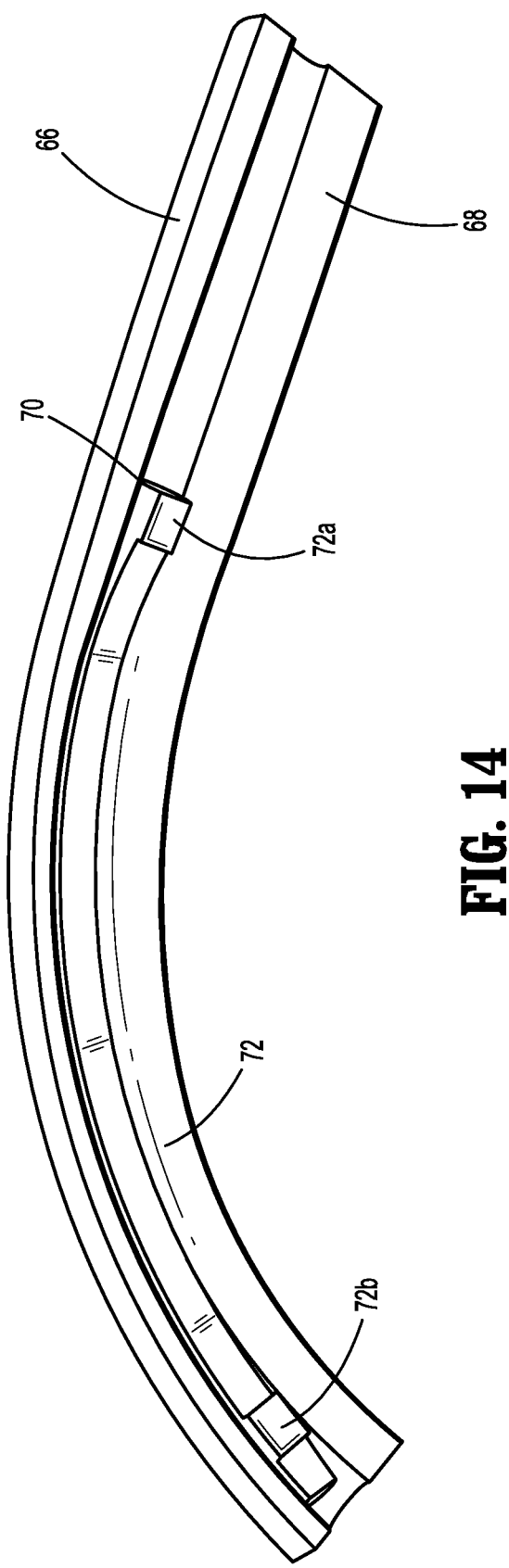
FIG. 14 is a bottom, perspective view of an interface member of the sensor assembly of FIG. 12.

With reference to FIGS. 12-14, a curved sensor assembly 60 includes a base housing 62, having first and second force sensing resistor assemblies 64 and 65 disposed within the base housing 62, and an interface member 66 disposed over the force sensing resistor assemblies 64 and 65. To avoid unnecessary repetition, only the differences between the sensor assembly 30 and the curved sensor assembly 60 are described below.

The first force sensing resistor assembly 64 is disposed at a first end portion 62a of the base housing 62 and the second force sensing resistor assembly 65 is disposed at a second end portion 62b of the base housing 62. The force sensing resistor assemblies 64 and 65 may be coupled to base housing 62 in the same manner as described above with respect to the base housing 32 and may include contacts (not shown) extending through the base housing 62 to electrically couple the force sensing resistor assemblies 64 and 65 to the control device 4. In addition, the base housing 62 may be coupled to curved base 105 of the first link 104 in a similar manner as the base housing 32 as described above.

The force sensing resistor assemblies 64 and 65 are substantially similar to the force sensing resistor assembly 34. In embodiments, the force sensing resistor assemblies 64 and 65 may have any suitable shape, including but not limited to rectangular or circular.

The interface member 66 has a substantially curved shape and includes a channel 70 defined on an inner surface 68 of the interface member 66. The channel 70 is configured to receive a bridge 72 therein. The bridge 72 may be formed from any rigid material, such as metals or rigid thermoplastic materials, such as those formed from polycarbonates and the like. The bridge 72 includes a protuberance 72a and 72b at each end thereof, which are configured to engage the first and second force sensing resistor assemblies 64 and 65, respectively, such that any force on the interface member 66 and the bridge 72 is applied to one or both of the force sensing resistor assemblies 64 and 65. The protuberances 72a and 72b may be separate parts that are fixed to the bridge 72 and made from an elastic material such as rubber, polymer, and the like to allow for self-alignment of the protuberances 72a and 72b contacting the force sensing resistor assemblies 64 and 65. The protuberances 72a and 72b may have any suitable shape, such as pads, fixed to the underside of the bridge 72 or o-rings fitted around the circumference of the bridge.

Figure 15:
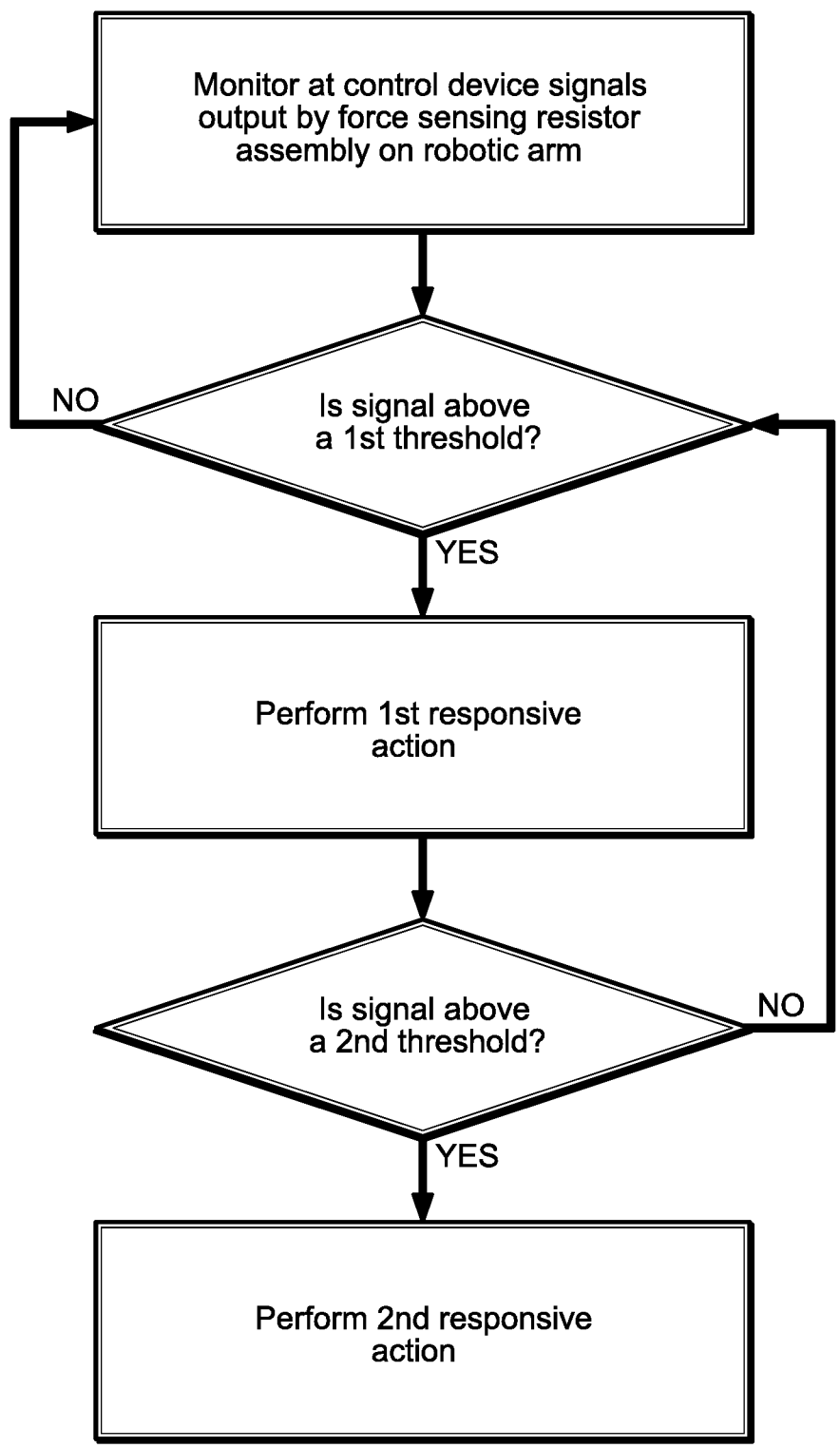
FIG. 15 is a flow chart of a method for controlling the surgical robotic arm according to the present disclosure.

With reference to FIG. 15, operation of the surgical robotic system 1 is described. The control device 4 continuously monitors signals from one or more sensor assemblies 100 and controls the robotic arm 2 in response to the signals output by one of the sensor assemblies 100.

In embodiments, the sensor assemblies 100 may continuously output a signal based on a minimum resistance of the sensor assemblies 100. The control device 4 may utilize this signal to verify electrical connectivity between the sensor assemblies 100 and the control device 4, e.g., due to cable failure or other electrical malfunctions.

The control device 4 is configured to calculate the force exerted on one or more sensor assemblies 100 (e.g., by using a transfer function or any other suitable method). The control device 4 may be programmed to perform a plurality of control functions on the robotic arm 2 based on the calculated force. In particular, the control device 4 may store one or more force thresholds, such that when the measured force exceeds the threshold, the control device 4 performs a programmed function. In embodiments, when the measured force exceeds a predetermined threshold, the control device 4 may stop any movement of the robotic arm 2 or at least one of the links 104, 106, and 108 of the robotic arm 2 that encounters the obstruction. The control device 4 may also output a warning (e.g., audio and/or visual alert) to the users. However, if the signals output by sensor assemblies 100 do not exceed any of the thresholds, the control device 4 continues to control the robotic arm 2 according to other routines and control functions.

In an embodiment, multiple round or straight force sensing resistor assemblies (e.g., force sensing resistor assemblies 34, 64 or 65) may be located under a single interface member (e.g., interface member 36 or 66), such as, for example, in a curved sensor assembly 60.

With continued reference to FIG. 15, after one of the sensor assemblies 100 is actuated, e.g., due to contact with an obstruction, a signal corresponding to the detected force is transmitted to the control device 4. The control device 4 determines the amount of force exerted on one of the sensor assemblies 100. The control device 4 then compares the force to a first threshold, which may be associated with partial contact between an obstruction and one or more sensor assemblies 100. This may be due to a surgical drape being bunched and pulled by the robotic arm 2. If the measured force exceeds the first threshold, the control device 4 may perform a cautionary action, such as output a warning. The signals from the sensor assemblies 100 are continuously monitored by the control device 4 and the warning may be output continuously while the calculated force is above the first threshold. If the calculated force exceeds a second threshold, which may correspond to more forceful contact with the obstruction, the control device 4 may perform a second action, such as stopping movement of the robotic arm 2 or one of its movable links 104, 106, and 108. It is envisioned that the above-described thresholds and algorithm may be stored in the memory of the control device 4 and the processor of the control device 4 is configured to execute instructions or programs embodying the above-described algorithm.

Figure 16A:
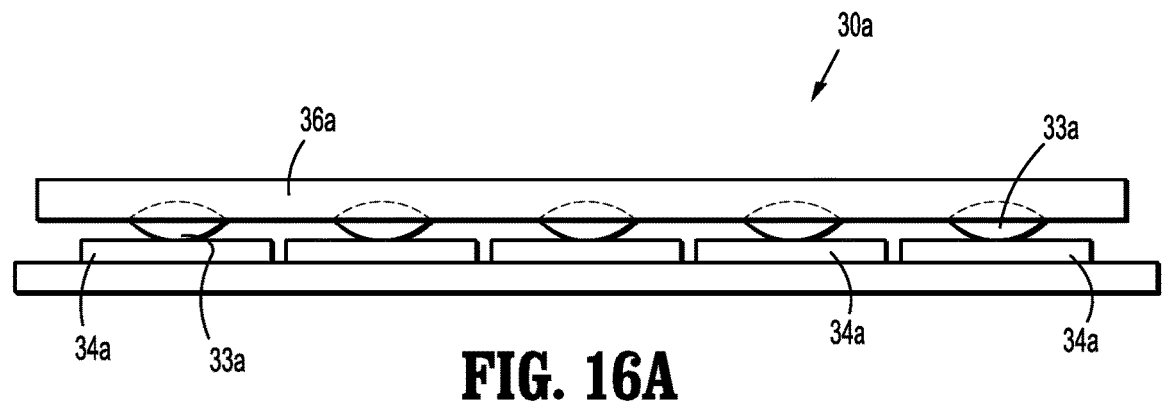
FIGS. 16A-16C are schematic illustrations of alternate embodiments of force sensor assemblies, in accordance with the present disclosure.

With reference to FIG. 16A, an alternate embodiment of a force sensor assembly, according to the present disclosure, is illustrated and generally designated with reference numeral 30A. Force sensor assembly 30A may include a plurality of separate, discrete force sensing resistor assemblies 34A, where rigid contact elements 33A are adhered to a bottom surface of interface member 36A or imbedded/anchored into interface member 36A, with a rigid contact element 33A directly contacting a respective force sensing resistor assemblies 34A.

Figure 16B:
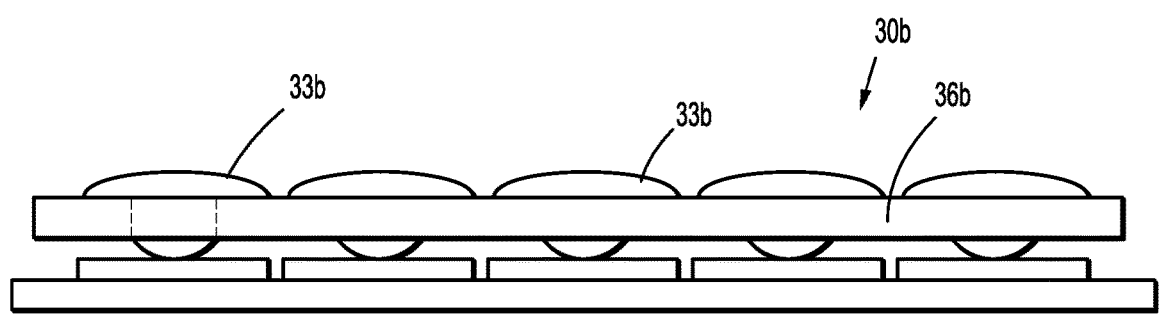

In another alternate embodiment, as illustrated in FIG. 16B, an alternate embodiment of a force sensor assembly, according to the present disclosure, is illustrated and generally designated with reference numeral 30B. Force sensor assembly 30B may include rigid elements 33B that may be imbedded in interface member 36B with the ends of rigid element 33B protruding out of both a bottom and a top surface of interface member 36B.

Figure 16C:
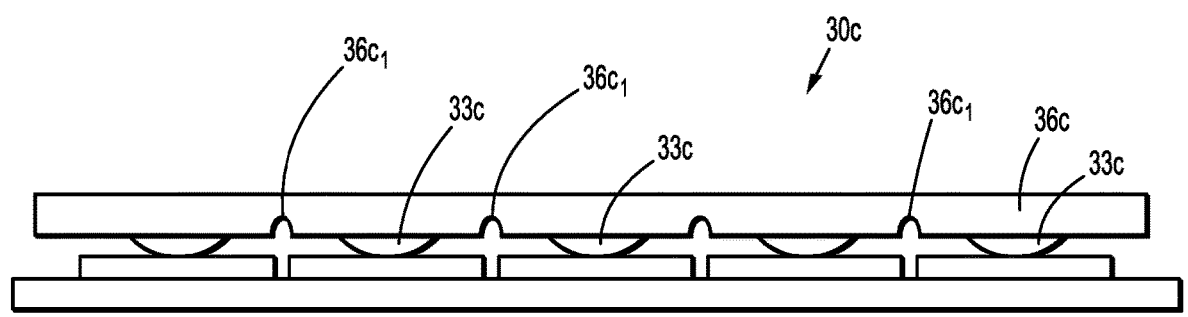
Figure 17A:
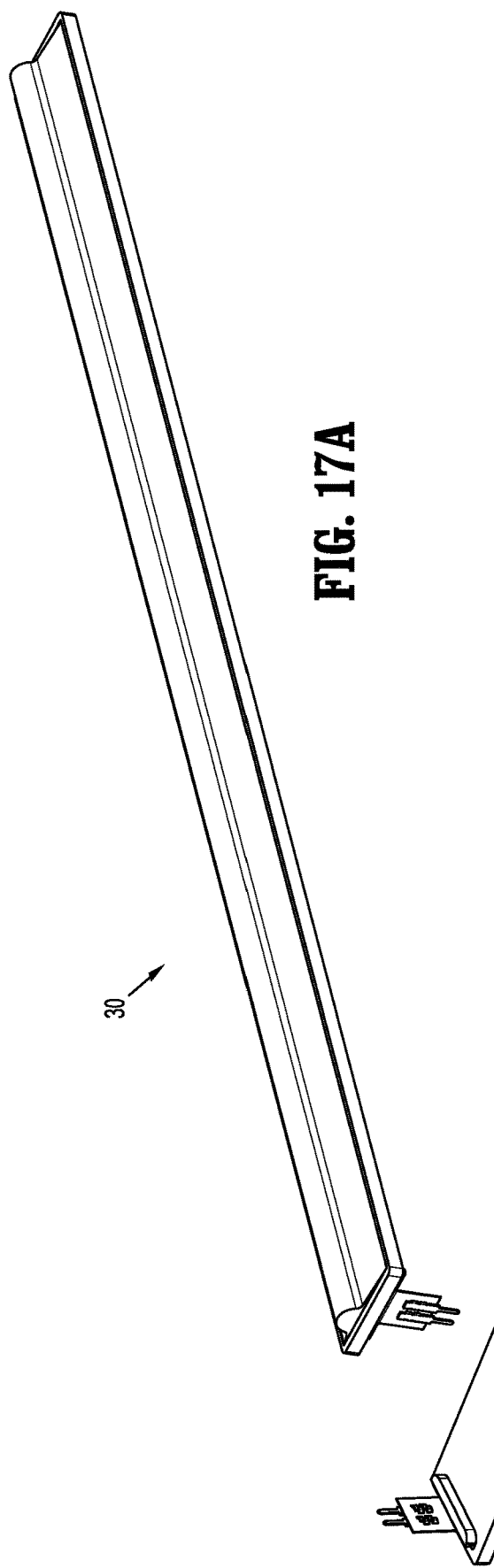
FIG. 17A is a top, perspective view of a sensor assembly according to an embodiment of the present disclosure.
Figure 17B:
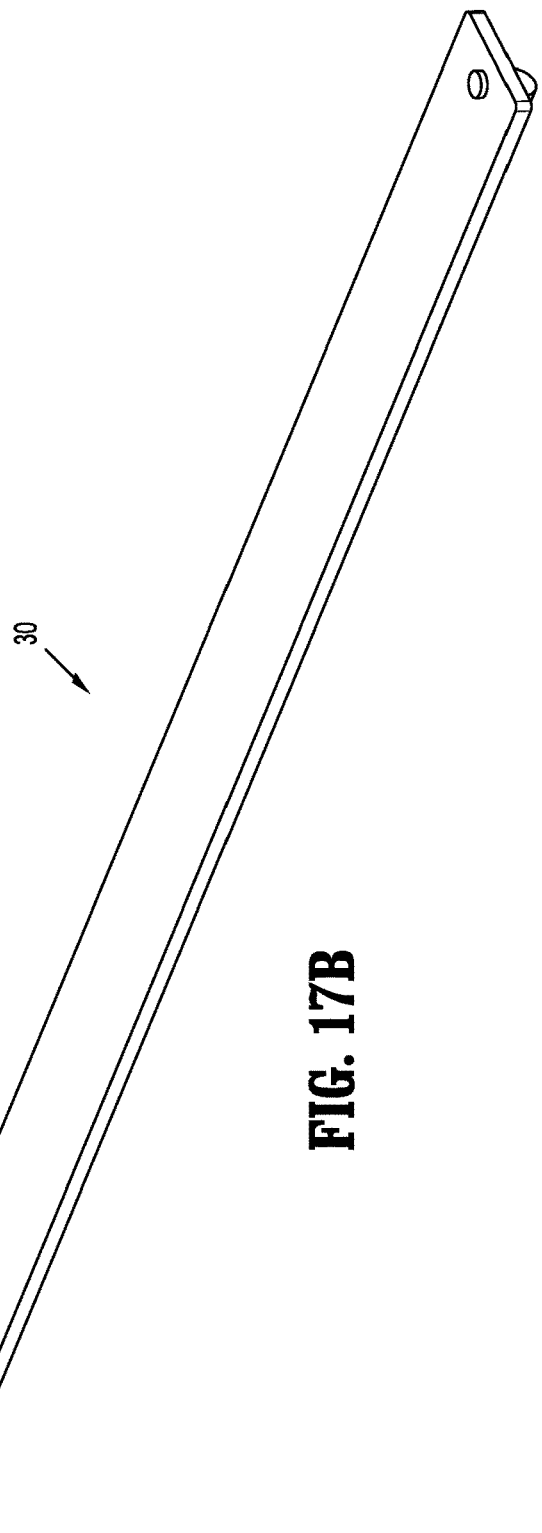
FIG. 17B is a bottom, perspective view of the sensor assembly of FIG. 17A.
Figure 17E:
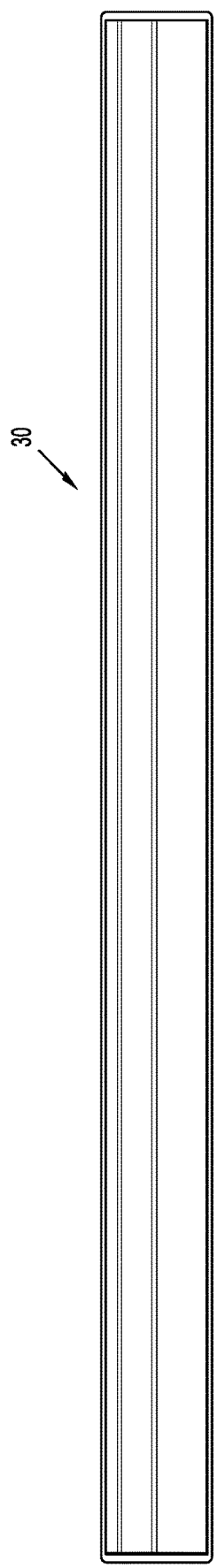
FIG. 17E is a top, plan view of the sensor assembly of FIG. 17A.
Figure 17F:
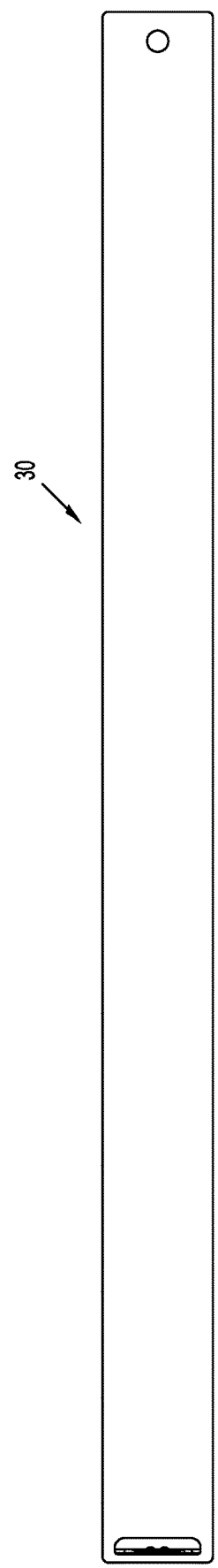
FIG. 17F is a bottom, plan view of the sensor assembly of FIG. 17A.
Figure 17G:
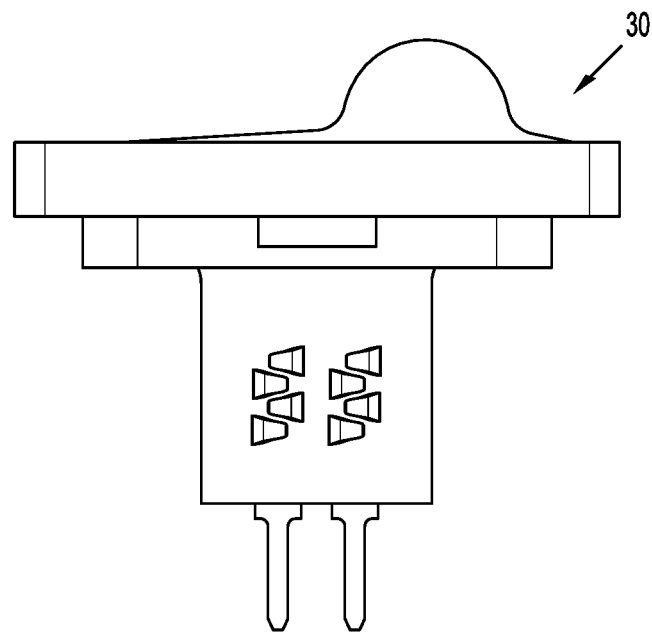
FIG. 17G is a front, elevation view of the sensor assembly of FIG. 17A.
Figure 17H:
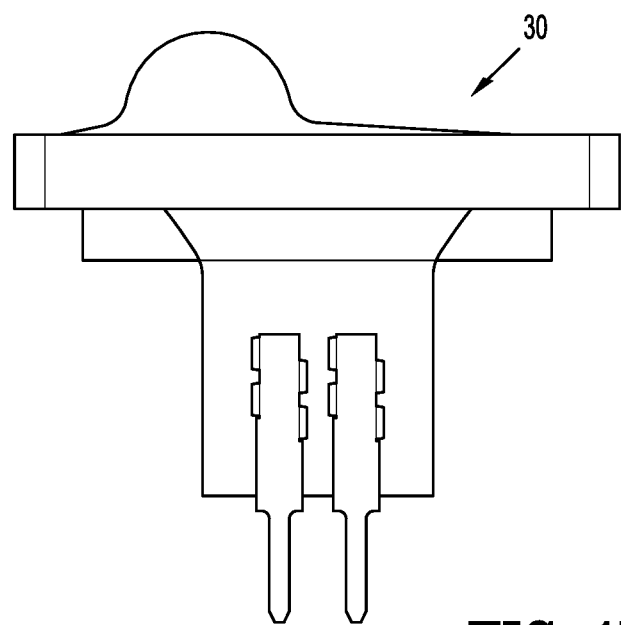
FIG. 17H is a rear, elevation view of the sensor assembly of FIG. 17A.
Figure 18G:
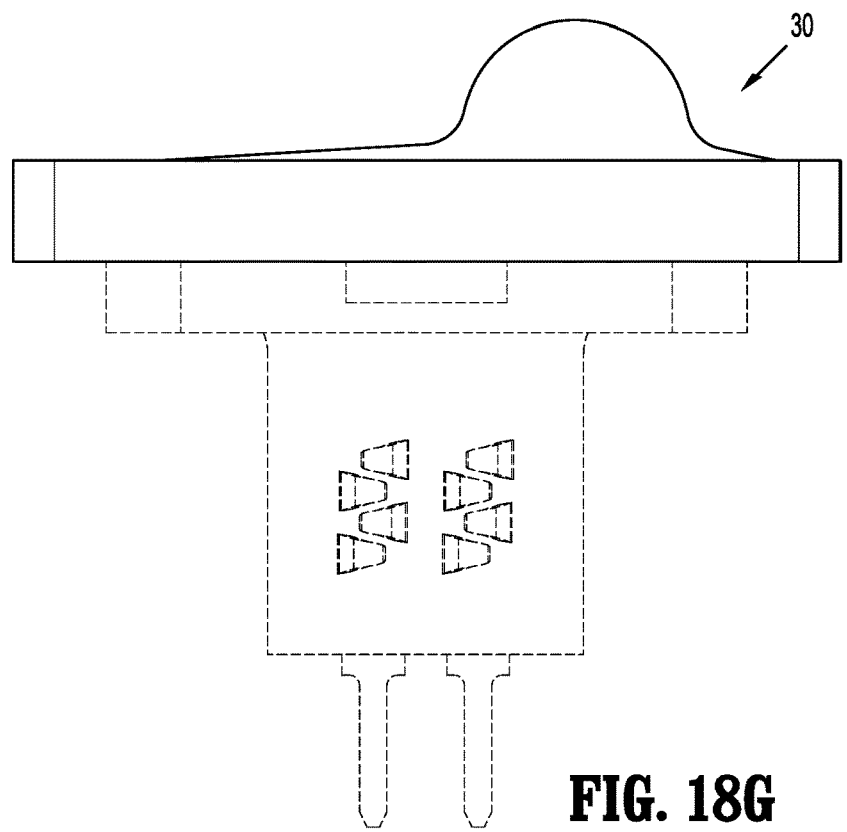
FIG. 18G is a front, elevation view of the sensor assembly of FIG. 18A.
Figure 18H:
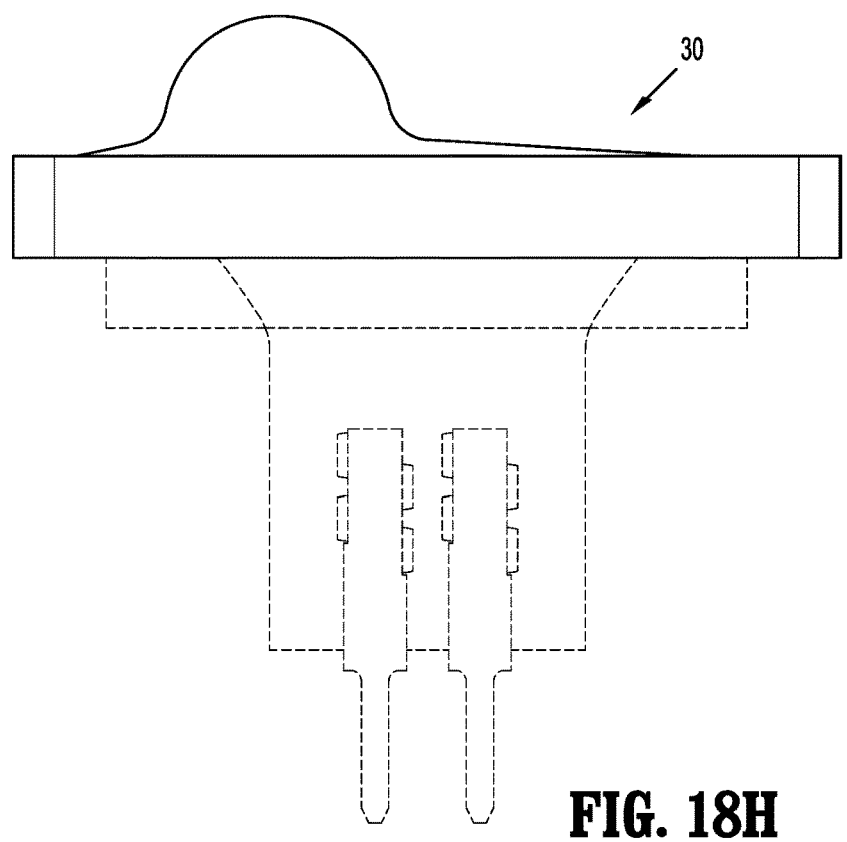
FIG. 18H is a rear, elevation view of the sensor assembly of FIG. 18A.
Figure 19E:
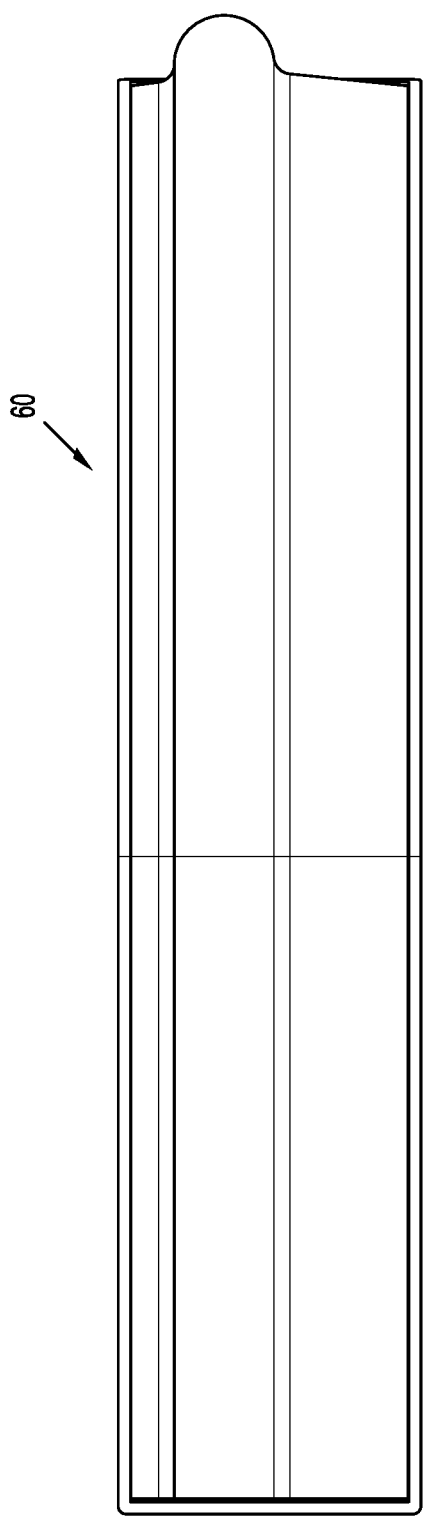
FIG. 19E is a top, plan view of the sensor assembly of FIG. 19A.
Figure 19F:
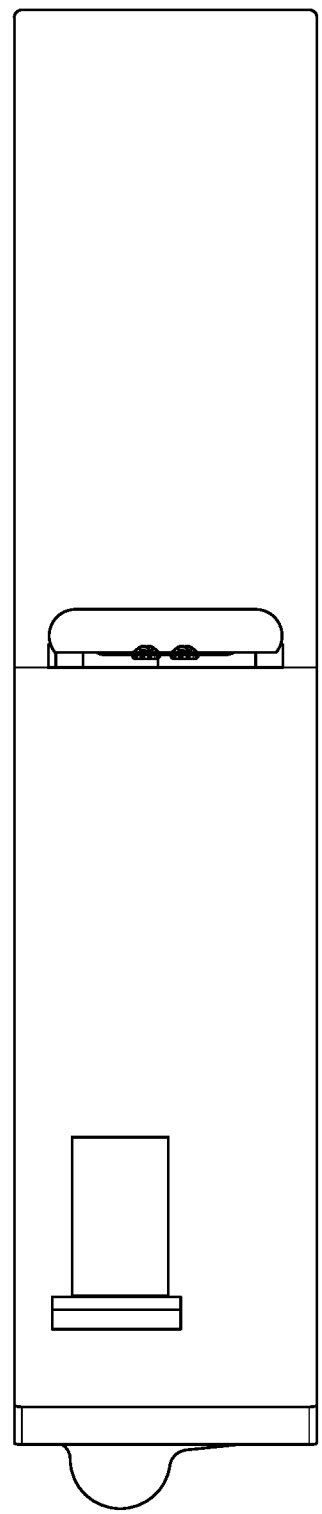
FIG. 19F is a bottom, plan view of the sensor assembly of FIG. 19A.
Figure 19G:
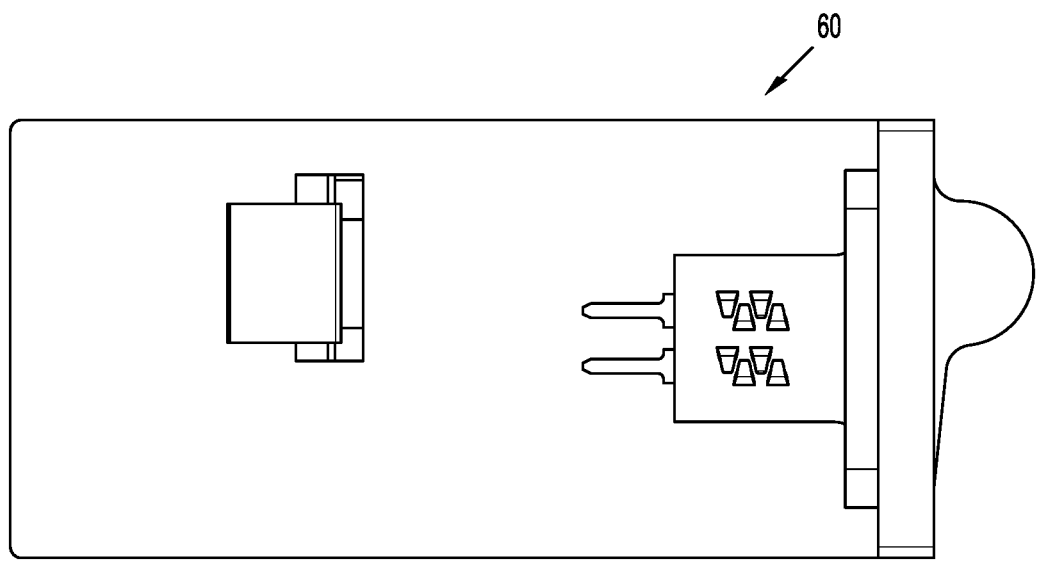
FIG. 19G is a front, elevation view of the sensor assembly of FIG. 19A.
Figure 19H:
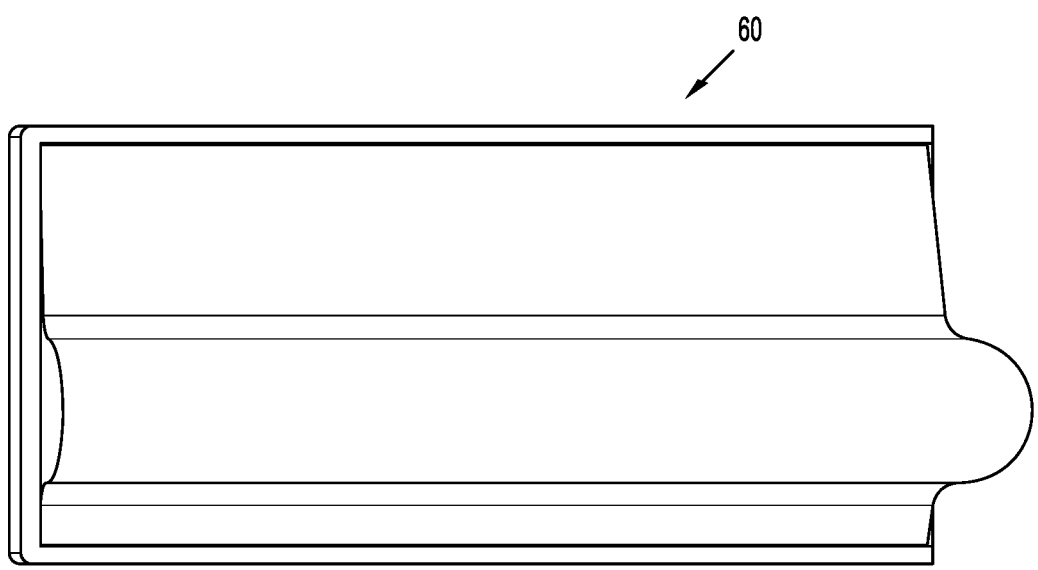
FIG. 19H is a rear, elevation view of the sensor assembly of FIG. 19A.
Figure 20C:
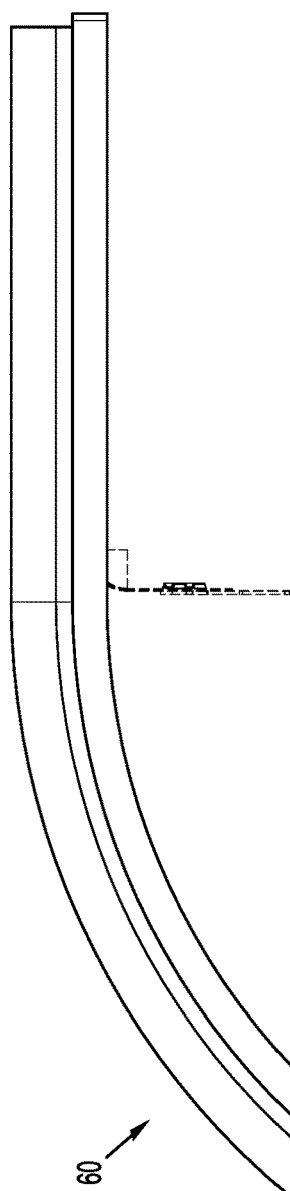
FIG. 20C is a right-side, elevation view of the sensor assembly of FIG. 20A.
Figure 20D:
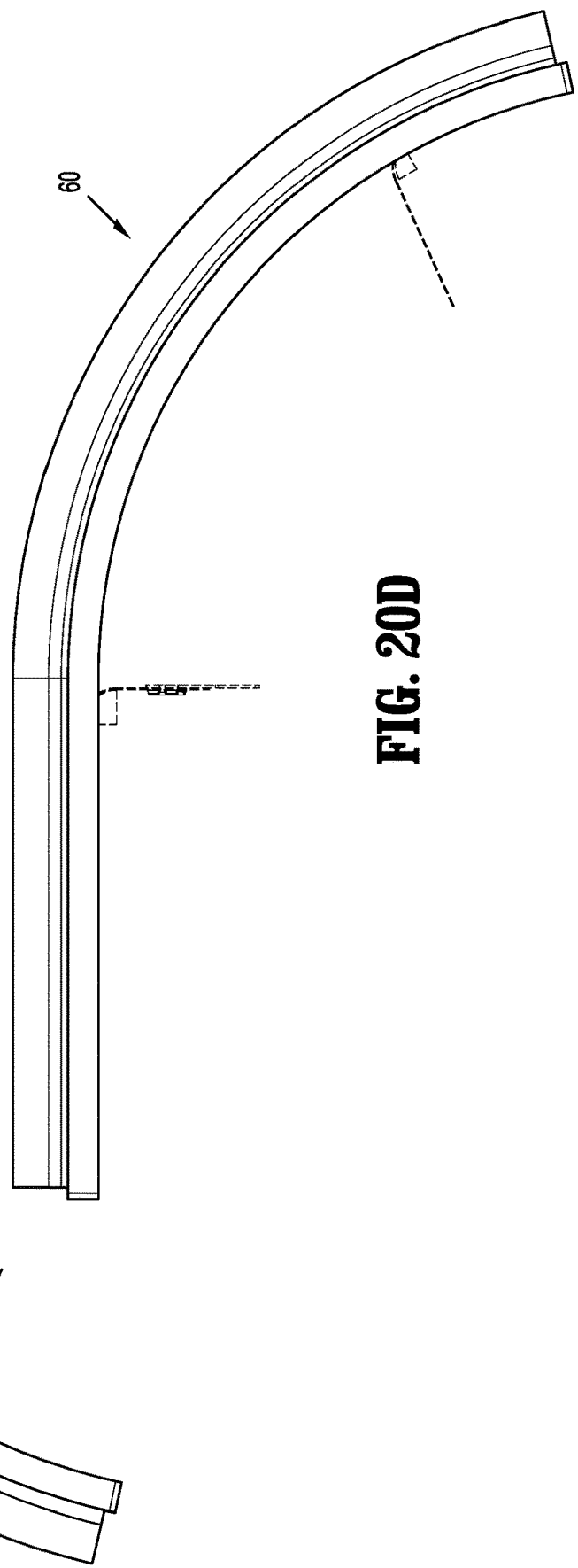
FIG. 20D is a left-side, elevation view of the sensor assembly of FIG. 20A.
Figure 20G:
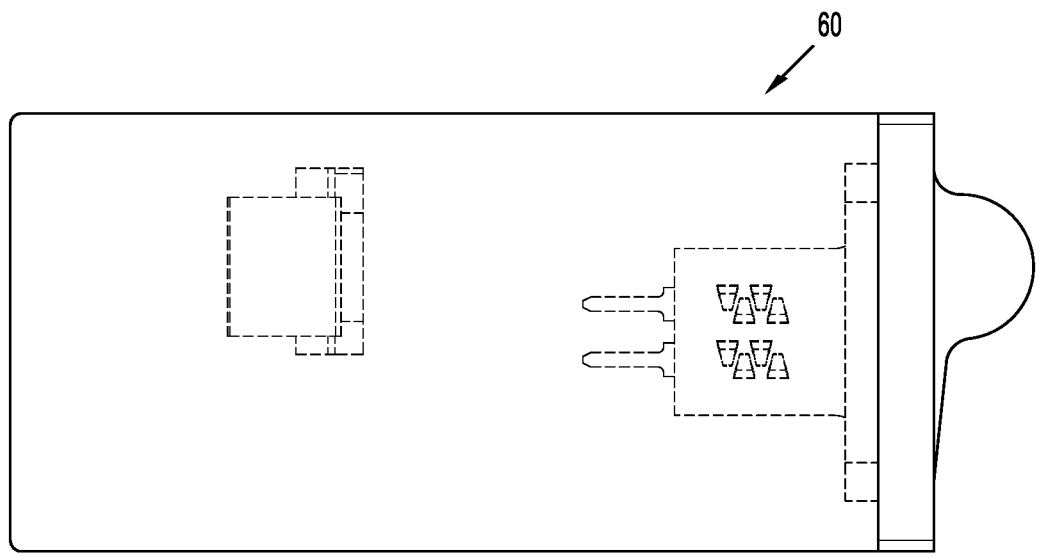
FIG. 20G is a front, elevation view of the sensor assembly of FIG. 20A.
Figure 20H:
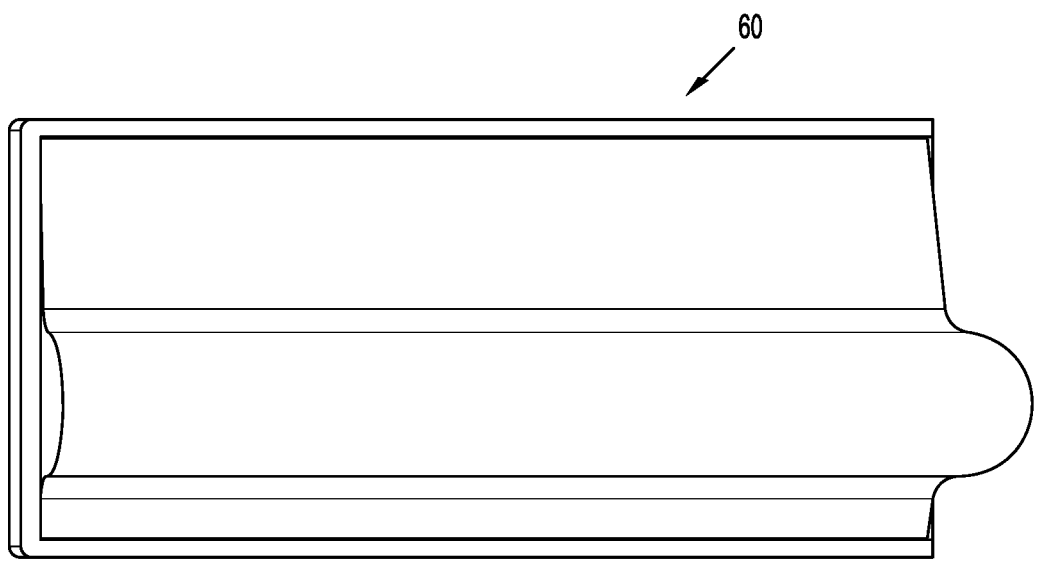
FIG. 20H is a rear, elevation view of the sensor assembly of FIG. 20A.
Figure 21:
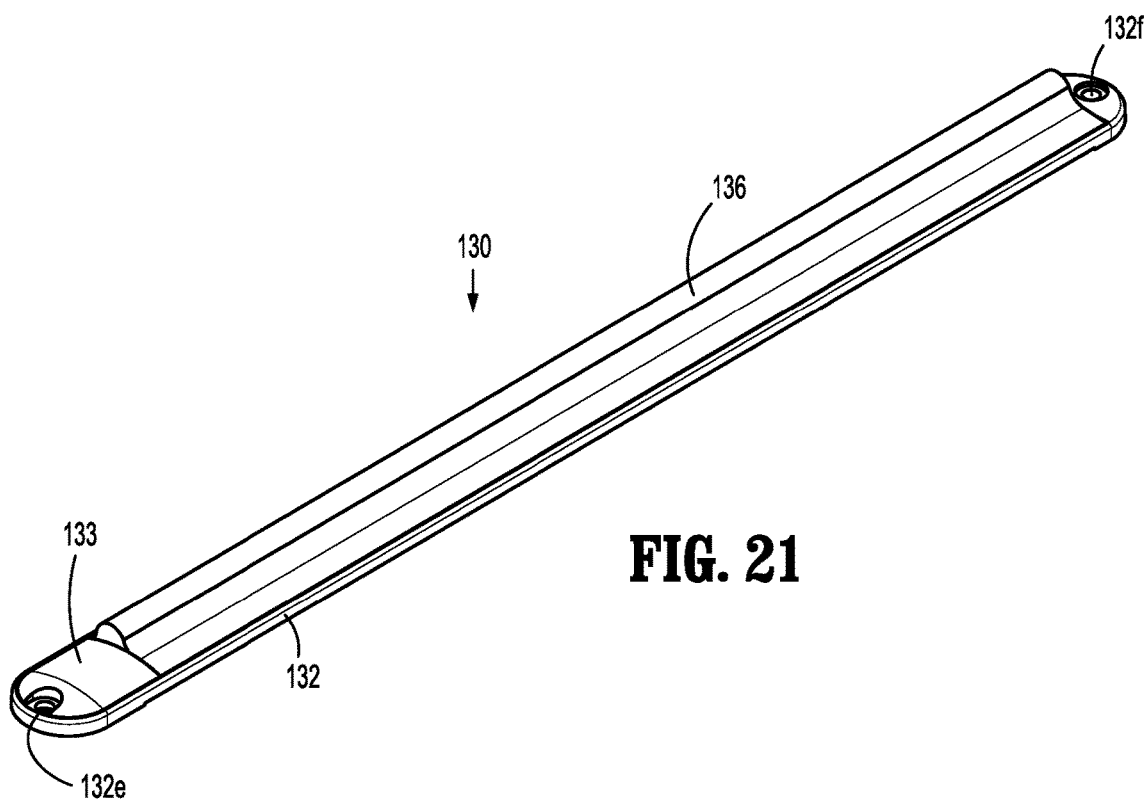
FIG. 21 is a top, perspective view of a straight sensor assembly disposed on surgical robotic arm of FIG. 2 according to one embodiment the present disclosure.

In yet another alternate embodiment, as illustrated in FIG. 16C, an alternate embodiment of a force sensor assembly, according to the present disclosure, is illustrated and generally designated with reference numeral 30C. Force sensor assembly 30C includes an interface member 36C having necking portions 36C (e.g., reduction in cross sectional area) disposed at selected locations along a length of interface member 36C to promote deformation of interface member 36C between rigid contact elements 33C.

In an embodiment, and in accordance with the present disclosure, it is contemplated that a surface area of inner protuberances 42 or contact elements 33A-33C, that makes contact with respective force sensing resistor assemblies, may vary along a length of the force sensor assembly to offer a corresponding variation in sensitivity along the length of the force sensor assembly. Similarly, in an embodiment, a distance from inner protuberance 42 and spacer 50 of the force sensing resistor assembly, can vary along the length of the force sensor assembly to offer corresponding variation in sensitivity along the length of the force sensor assembly.

FIGS. 17A-17H illustrate several views of sensor assembly 30; FIGS. 18A-18H illustrate several views of sensor assembly 30, with portions thereof in phantom; FIGS. 19A-19H illustrate several views of sensor assembly 60; and FIGS. 20A-20H illustrate several views of sensor assembly 60, with portions thereof in phantom.

FIGS. 21-26 illustrate a straight sensor assembly 130 according to another embodiment of the present disclosure. The sensor assembly 130 is substantially similar to the sensor assembly 30 of FIGS. 4-8 and only the differences between the sensor assembly 30 and the sensor assembly 130 are described below. The sensor assembly 130 includes a base housing 132 and a force sensing resistor ("FSR") assembly 134 disposed within the base housing 132. An interface member 136 is disposed over the FSR assembly 134. The sensor assembly 130 operates in a similar manner as the sensor assembly 30 in that the interface member 136, upon contacting an object, activates the FSR assembly 134, which outputs a signal indicating that contact has been made.

Figure 22:
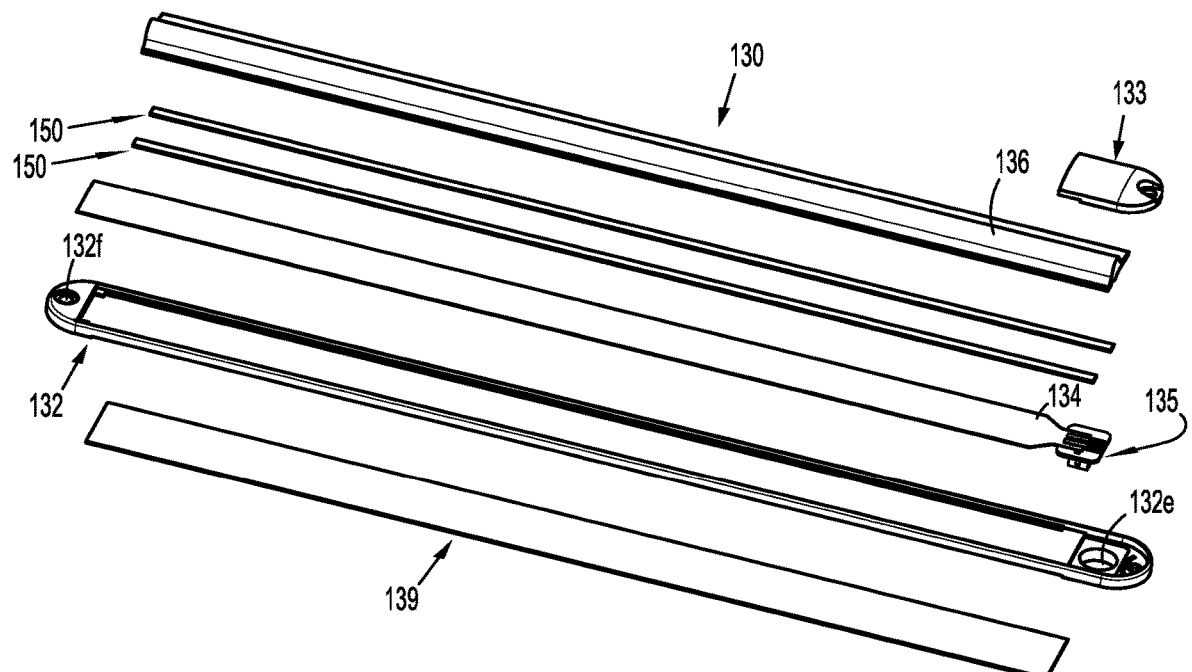
FIG. 22 is a perspective view of the sensor assembly of FIG. 21 with parts separated.
Figure 23:
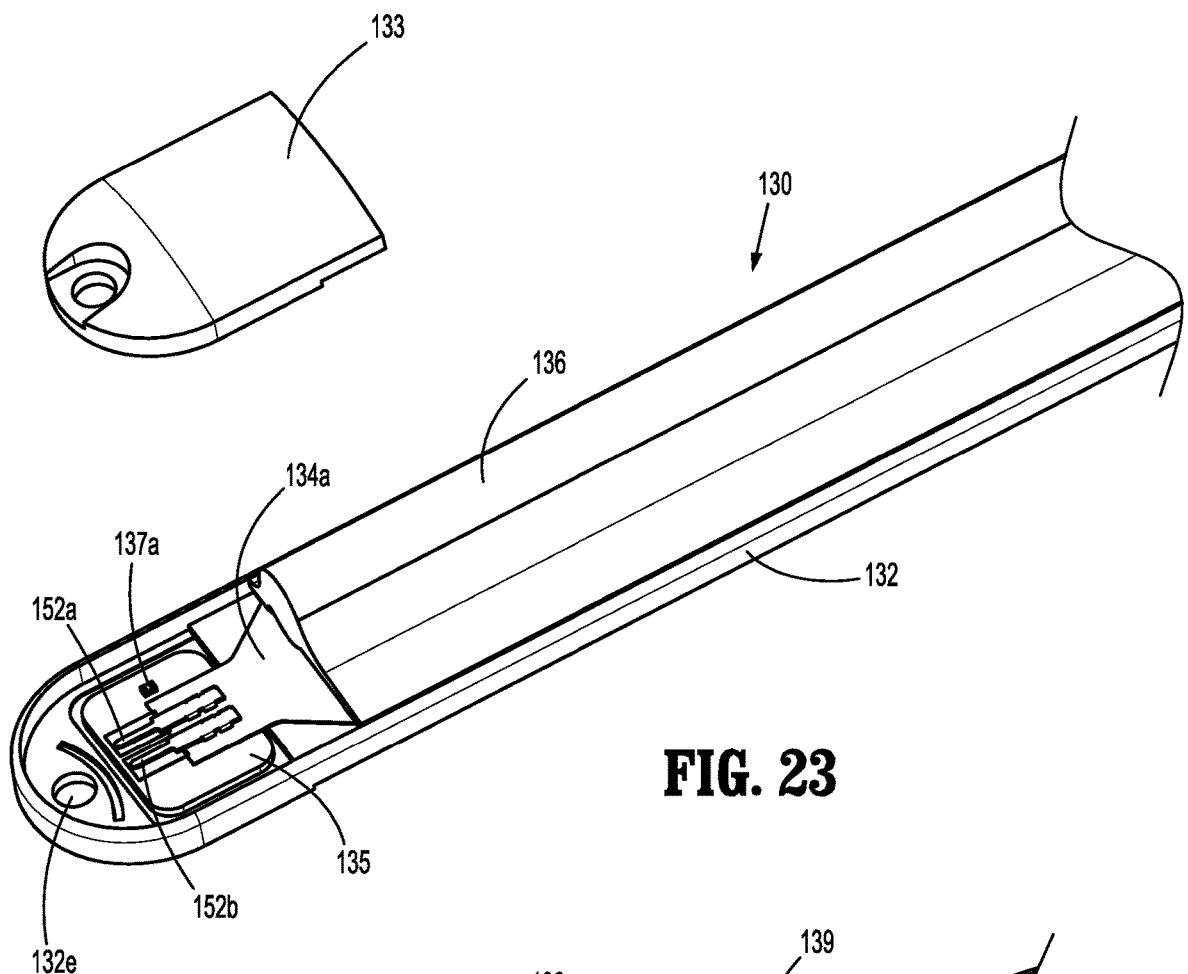
FIG. 23 is an enlarged, perspective view of the sensor assembly of FIG. 21 with parts separated.

The base housing 132 includes a lid 133 that encloses an end portion 134a of the FSR assembly 134 (FIG. 23). The base housing 132 includes a pair of openings 132e and 132f, which may be disposed at opposing ends of the base housing 132. The openings 132e and 132f are used for holding fasteners (not shown) for attaching the base housing 132 to the first, second, or third links 104, 106, or 108. In addition, the sensor assembly 130 may include an adhesive layer 139 (FIGS. 22 and 24) disposed on a bottom portion of the base housing 132 providing for another attachment point for the sensor assembly 130.

Figure 26:
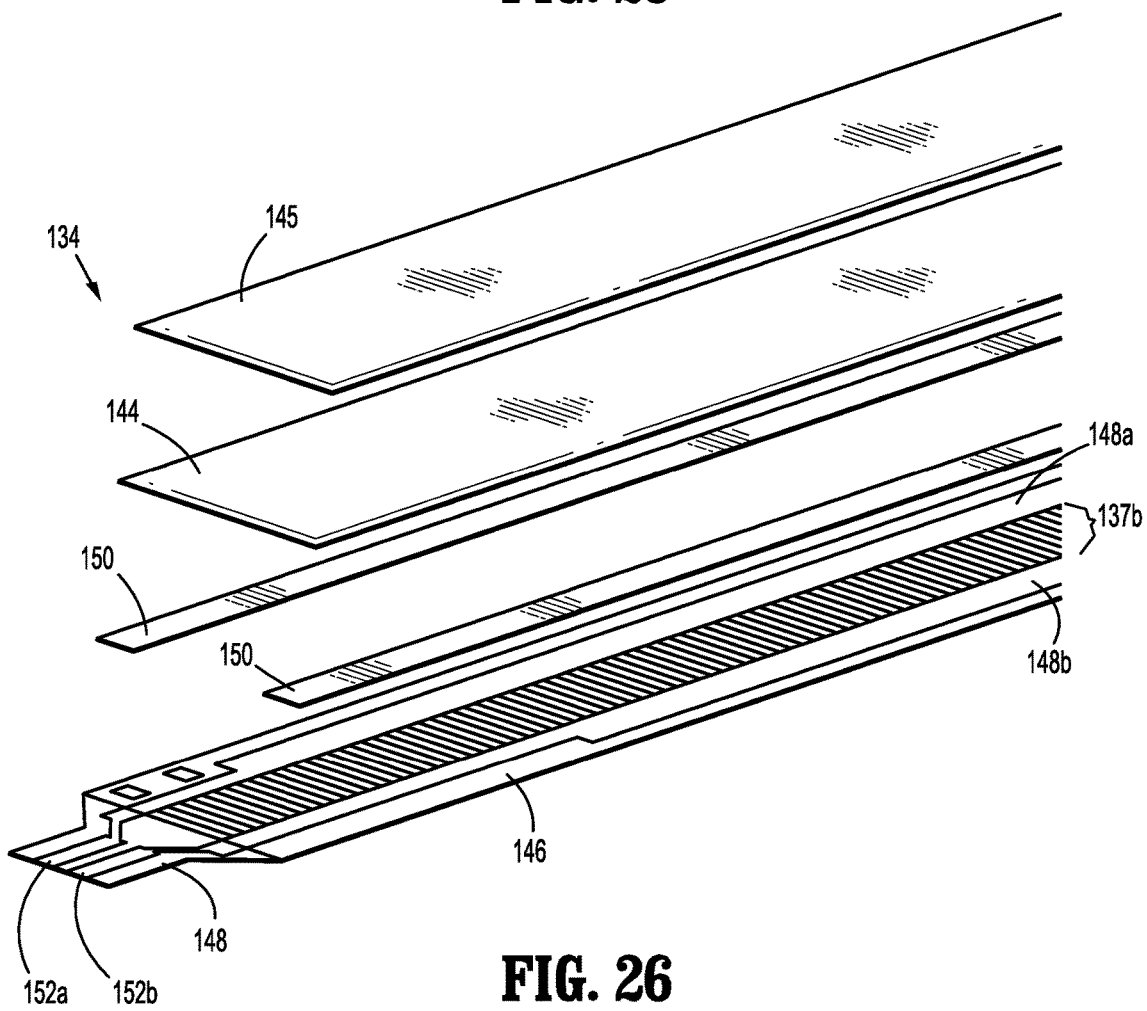
FIG. 26 is a perspective view of a force sensing resistor assembly of the sensor assembly of FIG. 21 with parts separated.
Figure 27:
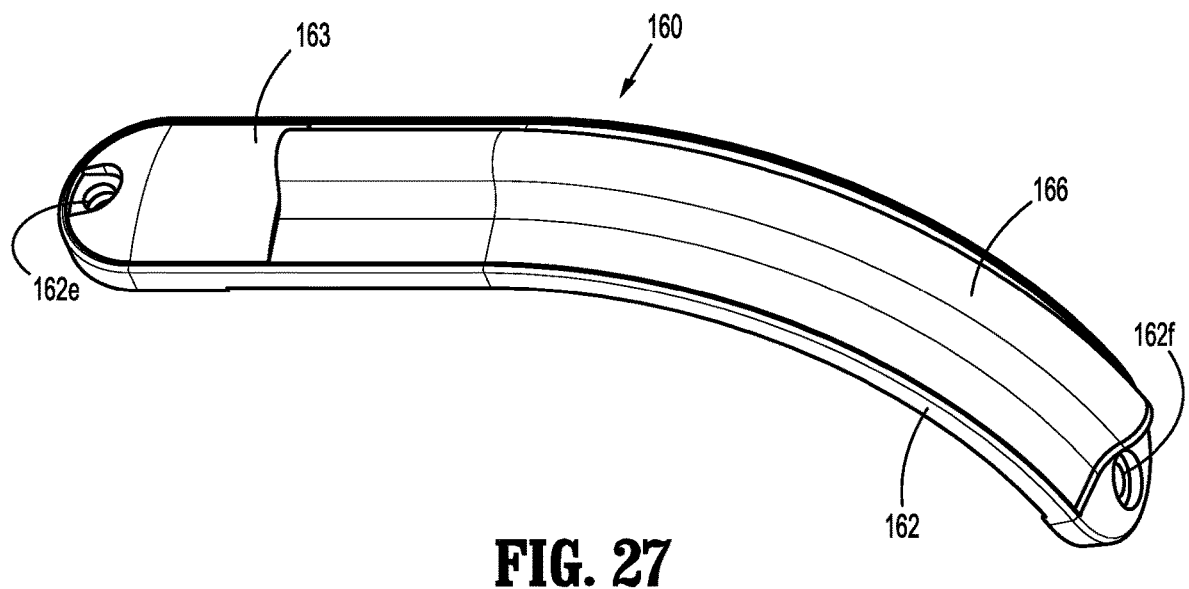
FIG. 27 is a top, perspective view of a curved sensor assembly disposed on surgical robotic arm of FIG. 2 according to one embodiment the present disclosure.

With reference to FIG. 26, the FSR assembly 134 includes an upper conductive layer 144, which may be formed from graphite or any other suitable conductive material. The upper conductive layer 144 is overlayed by an adhesive backing layer 145, which secures the upper conductive layer 144 to an underside of the interface member 136. The FSR assembly 134 also includes a pair of spacers 150, which may be double-sided adhesive tape. The spacers 150 separate the upper conductive layer 144 from a lower conductive substrate 146, such that the upper conductive layer 144 and the lower conductive substrate 146 do not incidentally contact each other unless the interface member 136 is contacted by external forces.

Figure 24:
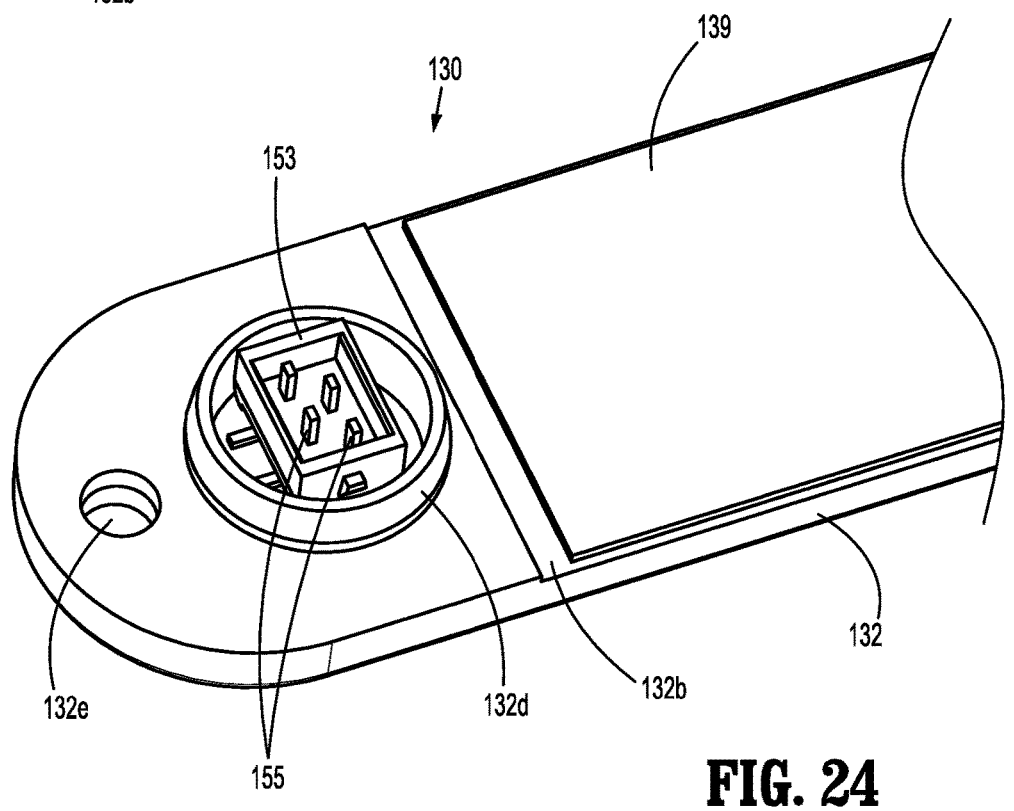
FIG. 24 is an enlarged, bottom, perspective view of the sensor assembly of FIG. 21.
Figure 25:
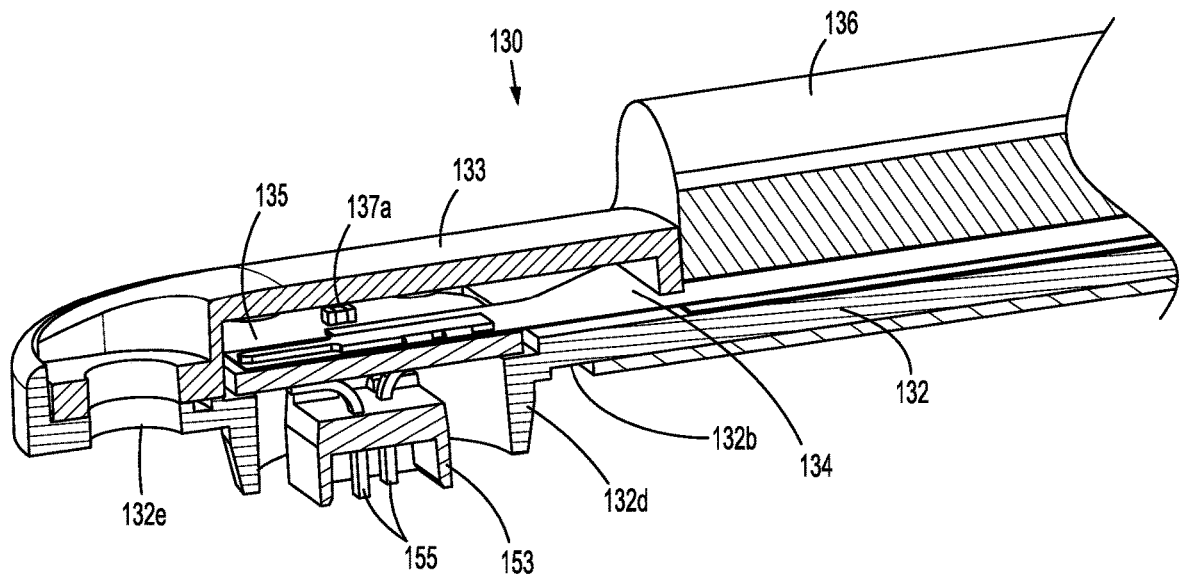
FIG. 25 is a longitudinal, cross-sectional view of the sensor assembly of FIG. 21.

The lower conductive substrate 146 may be a printed flexible circuit board including an interdigitated circuit 148 having a first electrode pattern 148a and a second electrode pattern 148b. Each of the first and second electrode patterns 148a and 148b terminates in respective contact members 152a and 152b that are electrically coupled to a printed circuit board ("PCB") 135 as shown in FIGS. 22, 23 and 25. The PCB 135 provides for placement of other electrical components, such as a resistor 137a (FIGS. 23 and 25). In addition, the PCB 135 secures the contact members 152a and 152b, each of which is electrically coupled to an electrical connector 153 having a plurality of pins 155 as shown in FIGS. 24 and 25. The connector 153 may be disposed within a surface projection 132d disposed on a bottom surface 132b of the base housing 132, thereby protecting the connector 153. The electrical connector 153 is configured to mate with a counterpart electrical connector (not shown) on the surgical robotic arm 2, providing for a secure electrical connection between the sensor assembly 130 and the surgical robotic arm 2.

In certain embodiments, the PCB 135 may not be fixedly secured within the base housing 132 providing the PCB 135 and the electrical connector 153 coupled thereto a certain degree of lateral movement along a surface of the base housing 132. This allows for the electrical connector 153 to align with a counterpart connector on the surgical robotic arm 2 during coupling of the sensor assembly 130 to the surgical robotic arm 2. In addition, the surgical robotic arm 2 may include a counterpart opening configured to accommodate the surface projection 132d. Thus the surface projection 132d provides physical protection to the connector 152 as well as orients and aligns the electrical connector 153.

The resistor 137a is coupled in parallel between the contact members 152a and 152b and provides a known finite resistance to an electrical circuit defined by the first and second electrode patterns 148a and 148b. The known resistance of the resistor 137a may be used to determine whether an electrical connection between the FSR assembly 134 and the surgical robotic arm 2 has been broken. In particular, the surgical robotic arm 2 is configured to output a sensor signal through the FSR assembly 134 during operation of the surgical robotic arm 2. Since the first and second electrode patterns 148a and 148b would not output an electrical signal unless contacted by the upper conductive layer 144, the surgical robotic arm 2 would not be able to distinguish between the FSR assembly 134 being disconnected and/or being non-functional since the FSR assembly 134 is designed as an open circuit that is closed by external contact. The presence of the resistor 137a alleviates this issue by providing a baseline resistance to the surgical robotic arm 2. Thus, whenever the first and second electrode patterns 148a and 148b are contacted by the upper conductive layer 144 due to external forces, the resistance would increase accordingly beyond the resistance of the resistor 137a signaling the surgical robotic arm 2 that external contact has been detected.

As shown in FIG. 26, the FSR assembly 134 may also include a second resistor 137b, which may be coupled between the first and second electrode patterns 148a and 148b. The second resistor 137b may also be disposed on a PCB, or in alternative embodiments, may be disposed on a flexible circuit of the lower conductive substrate 146 as shown in FIG. 26. Similarly, the second resistor 137b may also be coupled in parallel between the first and second electrode patterns 148a and 148b.

FIGS. 27-34 illustrate a curved sensor assembly 160 according to another embodiment of the present disclosure. The sensor assembly 160 is substantially similar to the sensor assembly 60 of FIGS. 12-14 and the sensor assembly 130 of FIGS. 21-26 and only the differences between the sensor assembly 160 and the sensor assemblies 60 and 130 are described below. The curved sensor assembly 160 includes a base housing 162, however, rather than having first and second FSR assemblies 64 and 65, the curved sensor assembly 160 includes a single FSR assembly 164 that is disposed within the base housing 62. An interface member 166 is also disposed over the force sensing resistor assembly 164.

Figure 29:
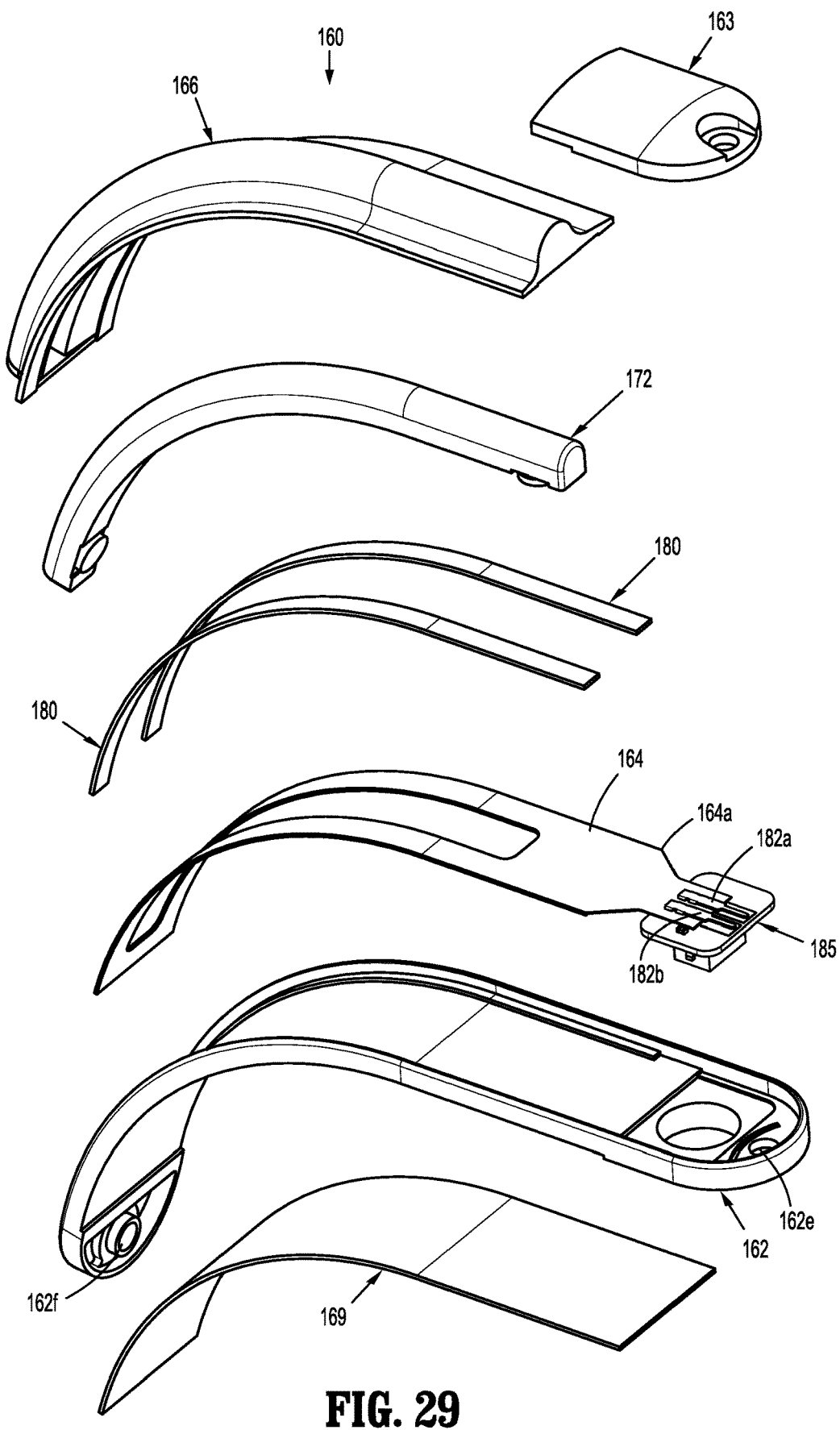
FIG. 29 is a perspective view of the curved sensor assembly of FIG. 27 with parts separated.

Similarly, to the base housing 132 of the sensor assembly 130, the base housing 162 includes a lid 163 that encloses an end portion 164a of the FSR assembly 164. The base housing 162 includes a pair of openings 162e and 162f as well as an adhesive layer 169 disposed on a bottom portion of the base housing 162 (FIG. 29).

Figure 34:
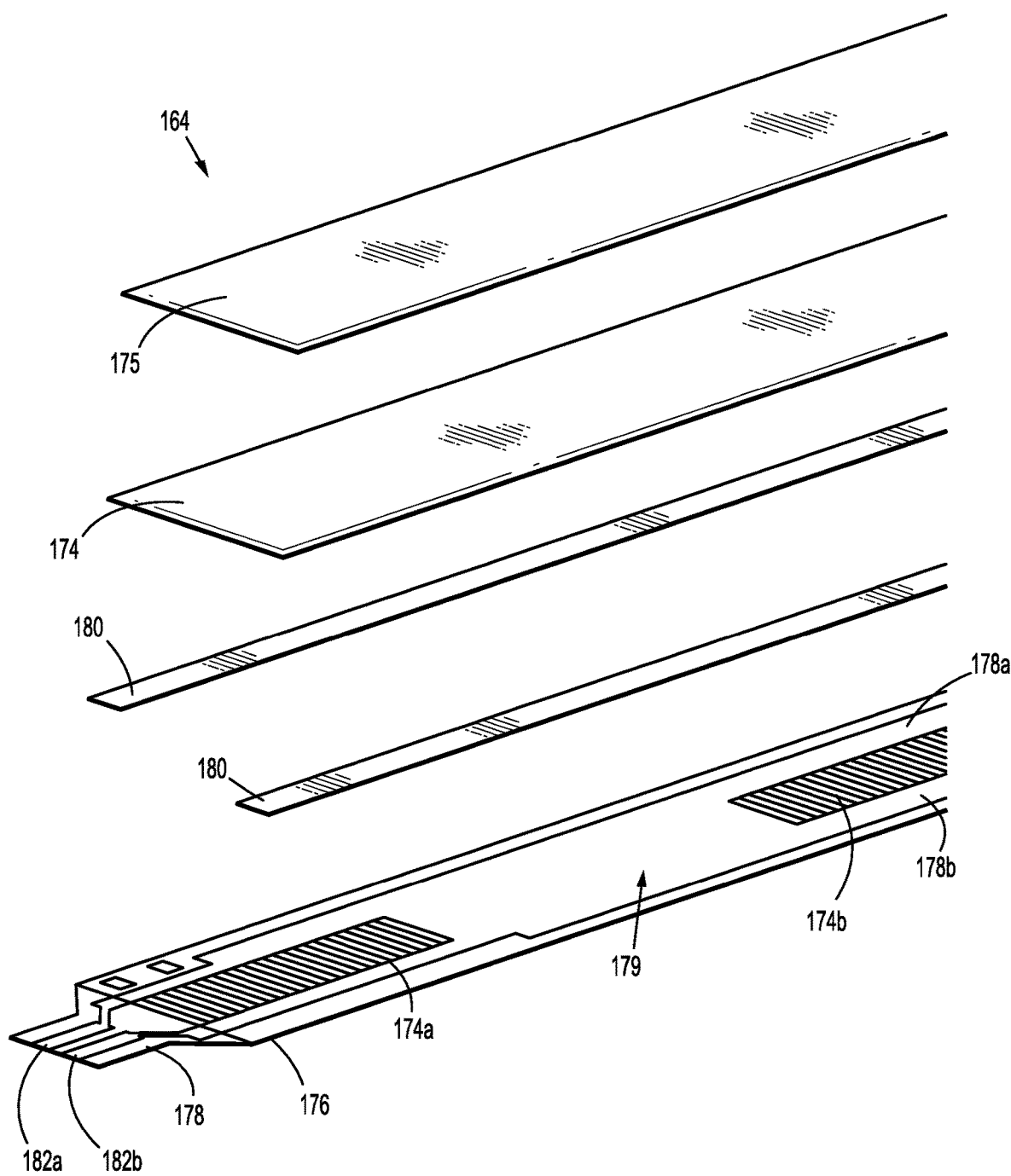
FIG. 34 is a perspective view of a force sensing resistor assembly of the sensor assembly of FIG. 27 with parts separated.

With reference to FIG. 34, the FSR assembly 164 is substantially similar to the FSR assembly 134 of the sensor assembly 130. Thus, the FSR assembly 164 also includes an upper conductive layer 174, an adhesive backing layer 175, a pair of spacers 180, and a lower conductive substrate 176.

Figure 33:
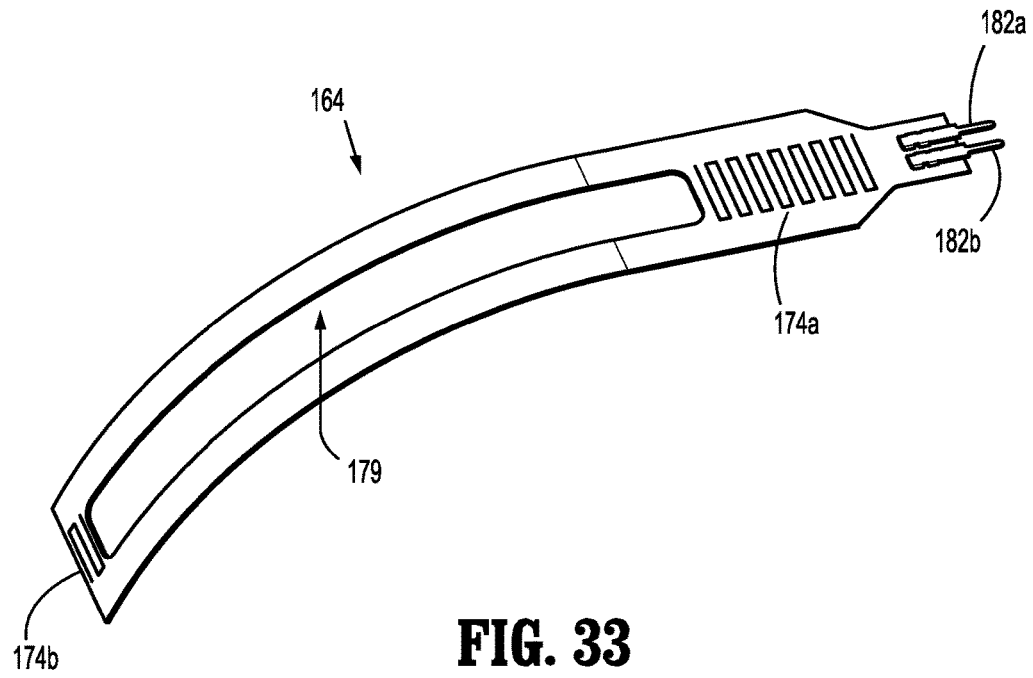
FIG. 33 is a perspective view of a force sensing resistor assembly of the curved sensor assembly of FIG. 27.

The lower conductive substrate 176 includes an interdigitated circuit 178 having a first electrode pattern 178a and a second electrode pattern 178b. The first and second electrode patterns 178a and 178b may define an opening 179 therebetween such that there are no finger electrodes at the opening 179. With reference to FIGS. 33 and 34, the finger electrodes of each of the first and second electrode patterns 178a and 178b are disposed at each of end portions 174a and 174b on either side of the opening 179. The opening 179 conforms to the curvature of the base housing 162, which allows for the FSR assembly 164 to be laid over a curved surface of the base housing 162 without affecting the reading of the FSR assembly 164 due to accidental contact of the finger electrodes of first and second electrode patterns 178a and 178b. The finger electrodes of the end portions 174a and 174b function normally and are laid over flat areas of the base housing 162.

The interface member 166 is substantially similar to the interface member 66 and also includes a curved shape and is configured to receive a bridge 172 therein. Similar to the bridge 72, the bridge 172 includes a pair of protuberances 172a and 172b at each end of the bridge 172. The protuberances 172a and 172b are configured to engage end portions 174a and 174b of the lower conductive substrate 176, respectively, such that any force on the interface member 166 and the bridge 172 is applied to the FSR assembly 164.

The protuberances 172a and 172b may be formed from any elastomeric material, which allows for the protuberances 172a and 172b to deform in response to the force applied on the bridge 172, thereby achieving a more uniform pressure on the first electrode pattern 178a and the second electrode pattern 178b and compensating for uneven contact surface of the protuberances 172a and 172b (e.g., which may exist due to low manufacturing tolerances).

Figure 28:
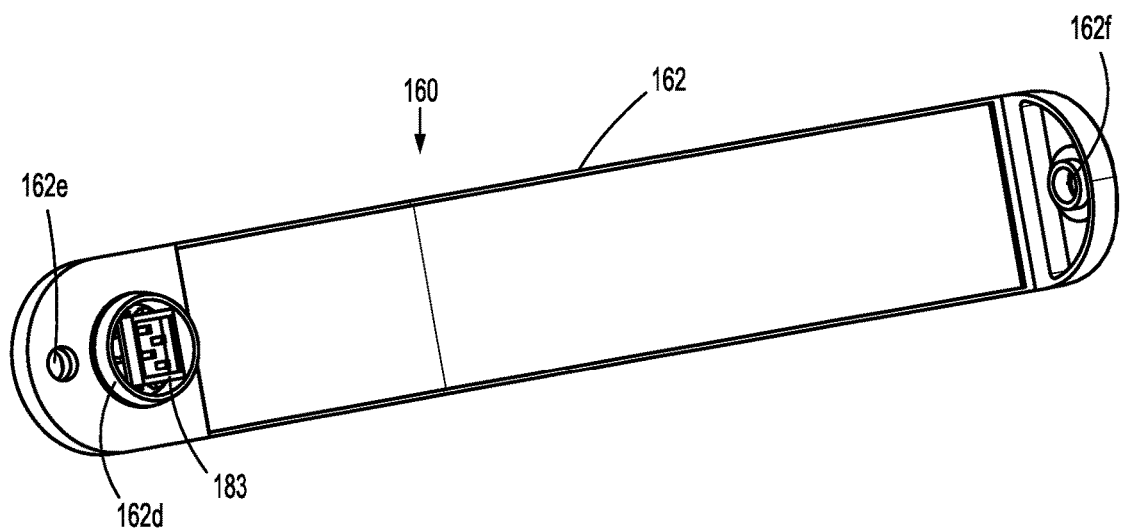
FIG. 28 is a bottom, perspective view of the curved sensor assembly of FIG. 27 according to one embodiment the present disclosure.
Figure 30:
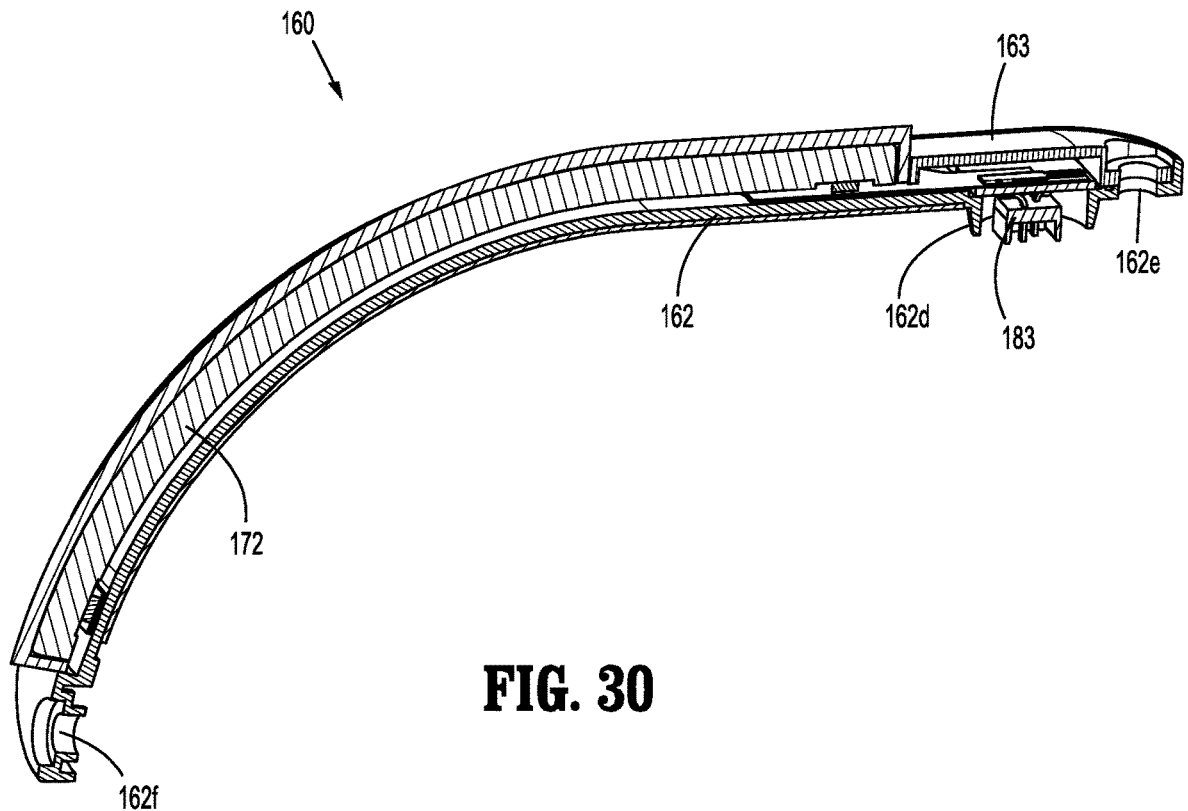
FIG. 30 is a longitudinal, cross-sectional view of the curved sensor assembly of FIG. 27.
Figure 31:
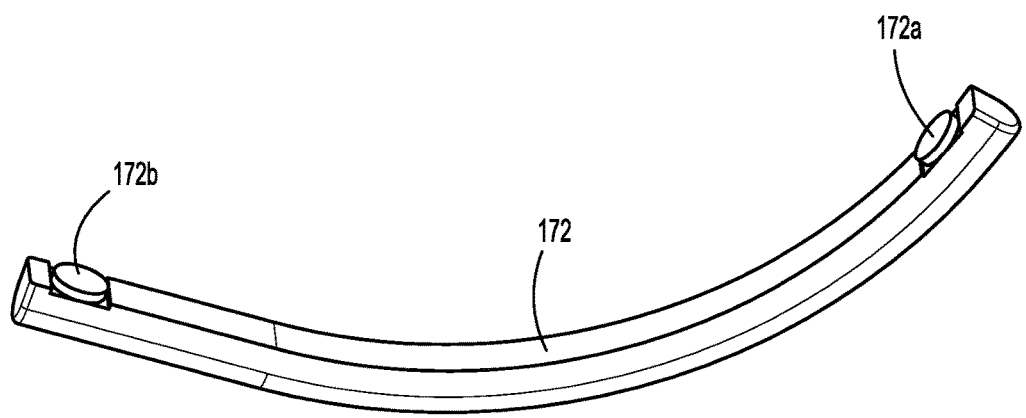
FIG. 31 is a perspective view of an interface member of the curved sensor assembly of FIG. 27.
Figure 32:
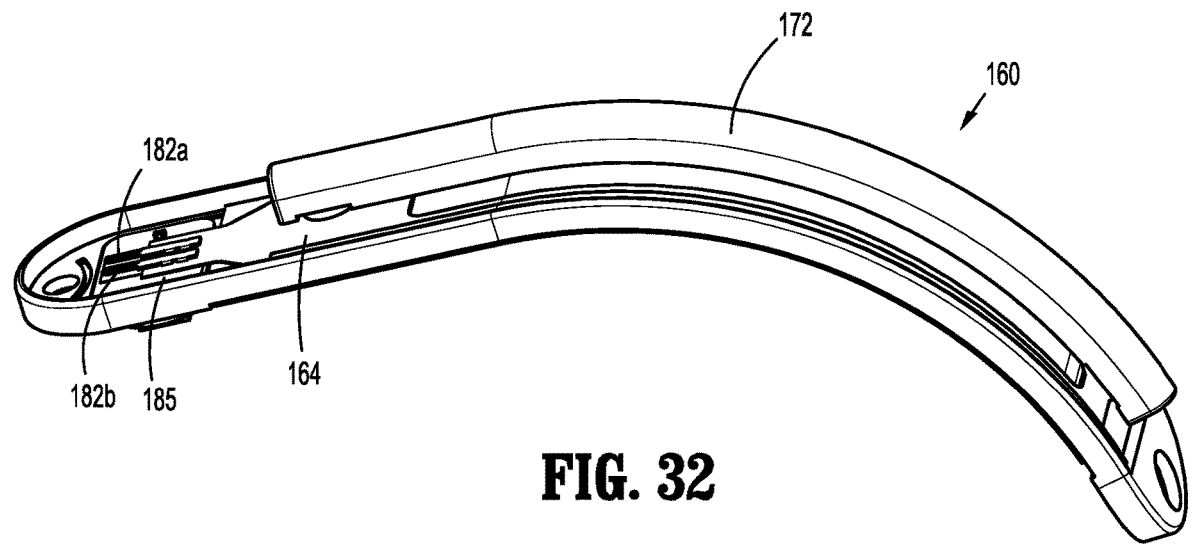
FIG. 32 is a perspective view of the curved sensor assembly of FIG. 27 with an outer layer removed.

As shown in FIGS. 29 and 32-34, each of the first and second electrode patterns 178a and 178b terminates in respective contact members 182a and 182b that are electrically coupled to a printed circuit board ("PCB") 185, which is substantially similar to the PCB 135. The PCB 185 is also coupled to an electrical connector 183 that is disposed within a projection 162d as shown in FIGS. 28 and 30. The electrical connector 183 is also movable within the projection 162d allowing for alignment with a counterpart connector on the surgical robotic arm 2 during coupling of the sensor assembly 160 to the surgical robotic arm 2.

Figure 35:
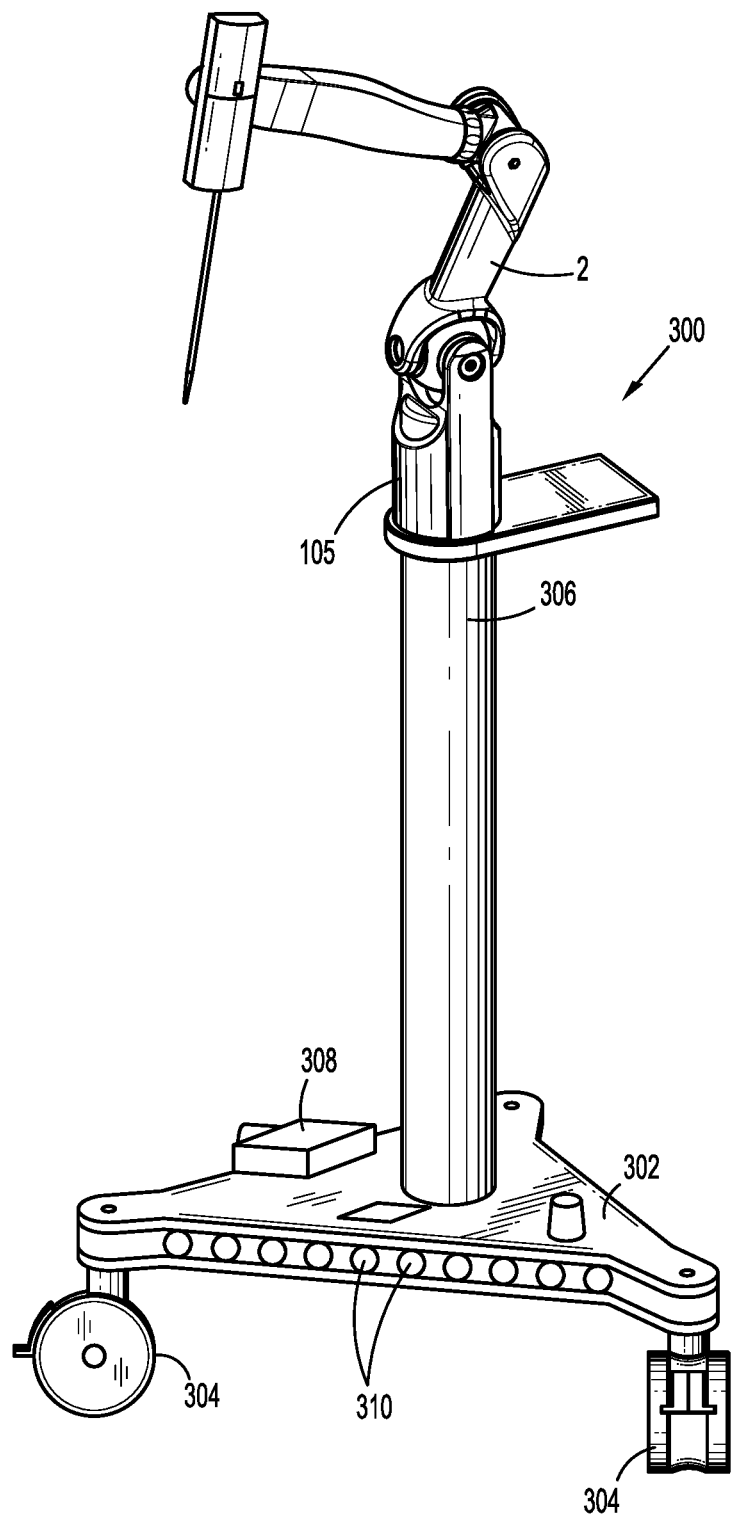
FIG. 35 is a perspective view of the surgical robotic arm of FIG. 2 disposed on a movable cart according to an embodiment of the present disclosure.

With reference to FIG. 35, the robotic arm 2 may be mounted to a cart 300 having a base 302 and a plurality of wheels 304. The cart 300 includes a support mount 306 for attaching the robotic arm 2. The curved base 105 of the robotic arm 2 (FIG. 2) may be attached to the support mount 306, which mechanically secures the robotic arm 2 to the cart 300 and provides for electrical connectivity to the robotic arm 2 from the control device 4 (FIG. 1). The base 302 also includes a controller 308 configured to interface with the robotic arm 2 and the control device 4.

In addition, the cart 300 also includes one or more lights 310. The lights 310 may be disposed around a perimeter of the base 302 and may be on at all times during use of the base 302 to increase its visibility. In embodiments, the lights 310 may be color-changing, dimmable light emitting diodes such that the controller 308 may adjust color and/or brightness/intensity of the lights 310. In addition to controlling lighting for visibility, the controller 308 may adjust the lighting pattern of the lights 310 to provide an indicator status of the robotic arm 2, such as green to denote normal operation, yellow to denote an issue with the robotic arm 2, etc. In addition, the lights 310 may also be operated in blinking patterns to provide additional feedback to the user.

In embodiments, the controller 308 is configured to communicate with the sensor assemblies 100 of the robotic arm 2, such that upon encountering a physical obstruction the controller 308, along with the control device 4, is notified of the event as disclosed above with respect to FIG. 15. In response to this event, the controller 308 is configured to control the lights 310 to indicate that the robotic arm 2 has encountered an obstruction. In embodiments, the lights 310 may output a red light and/or blink. This audio visual alarm may be output concurrently with actions executed by the control device 4, such outputting warnings on the operating console 5, stopping movement of the robotic arm 2, and the like.

In accordance with the present disclosure, it is envisioned and contemplated that any of the above embodiments may be applied to a sensor fixed to a curved or uneven surface. While force sensing resistor assemblies have been disclosed herein in detail, it is contemplated that other types of sensors may be used in a sensor assembly and applied to members of a robotic arm, to achieve the same or similar purposes described above. Such other sensors include and are not limited to strain gauges, piezoelectric sensors, limit switches, and the like.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

The invention claimed is:

1. A surgical robotic arm comprising:
a first link including a housing having an exterior surface;
a second link, wherein at least one of the first link or the second link is movable relative to each other; and
a sensor assembly coupled to the exterior surface of the housing of the first link, the sensor assembly including:
a base housing coupled to the exterior surface of the housing of the first link;
at least one force sensing resistor assembly disposed within the base housing and configured to measure force; and
an interface member disposed over the force sensing resistor assembly, the interface member configured to engage the at least one force sensing resistor assembly due to the interface member contacting an obstruction.

2. The surgical robotic arm according to claim 1, wherein the at least one force sensing resistor includes an upper conductive layer and a lower conductive substrate, the upper conductive layer configured to contact the lower conductive substrate in response to engagement with the interface member.

3. The surgical robotic arm according to claim 2, wherein an amount of contact between the upper conductive layer and the lower conductive substrate is representative of the measured force.

4. The surgical robotic arm according to claim 1, wherein the interface member includes an outer protrusion and an inner protrusion.

5. The surgical robotic arm according to claim 4, wherein the outer protrusion is offset from a center of the at least one force sensing resistor assembly.

6. The surgical robotic arm according to claim 1, wherein the sensor assembly is curved and the at least one force sensing resistor assembly includes a first force sensing resistor assembly disposed at a first end portion of the sensor assembly and a second force sensing resistor assembly disposed at a second end portion of the sensor assembly.

7. The surgical robotic arm according to claim 6, wherein the interface member is curved and includes a rigid bridge configured to engage at least one of the first force sensing resistor assembly or the second force sensing resistor assembly due to the interface member contacting an obstruction.

8. The surgical robotic arm according to claim 1, wherein the sensor assembly is curved and the at least one force sensing resistor includes a first end portion and a second portion and defines an opening therebetween.

9. The surgical robotic arm according to claim 8, wherein the interface member is curved and includes a rigid bridge configured to engage at least one of the first end portion or the second portion of the force sensing resistor assembly due to the interface member contacting an obstruction.

10. A surgical robotic system comprising:
a surgical robotic arm including:
  a first link including a housing having an exterior surface;
  a second link, wherein at least one of the first link or the second link is movable relative to each other; and
  a sensor assembly coupled to the exterior surface of the housing of the first link, the sensor assembly including:
    a base housing coupled to the exterior surface of the housing of the first link;
    a force sensing resistor assembly disposed within the base housing and configured to measure force; and
    an interface member disposed over the force sensing resistor assembly, the interface member configured to engage the force sensing resistor assembly in response to contacting an obstruction; and
a control device coupled to the surgical robotic arm and the sensor assembly, the control device configured to control movement of the surgical robotic arm based on the force measured by the force sensing resistor assembly.

11. The surgical robotic system according to claim 10, wherein the force sensing resistor includes an upper conductive layer and a lower conductive substrate, the upper conductive layer configured to contact the lower conductive substrate in response to engagement with the interface member.

12. The surgical robotic system according to claim 11, wherein an amount of contact between the upper conductive layer and the lower conductive substrate is representative of the measured force.

13. The surgical robotic system according to claim 10, wherein the control device is configured to determine connectivity of the force sensing resistor to the control device.

14. The surgical robotic system according to claim 10, wherein the control device includes:
a memory storing a set of instructions; and
a processor configured to execute the set of instructions.

15. The surgical robotic system according to claim 14, wherein the memory stores a force threshold.

16. The surgical robotic system according to claim 15, wherein the control device is configured to:
compare the force measured by the force sensing resistor assembly to the force threshold; and
control at least one of the first link or the second link based on a comparison of the force measured by the force sensing resistor assembly to the force threshold.

17. The surgical robotic system according to claim 10, wherein the sensor assembly includes at least one resistor coupled to the sensor assembly.

18. The surgical robotic system according to claim 17, further comprising a printed circuit board coupled to the sensor assembly and a connector coupled to the printed circuit board.

19. The surgical robotic system according to claim 18, wherein the connector is movably disposed within a projection on a bottom surface of the sensor assembly, the projection configured to mate with the at least one of the first link or the second link.

20. The surgical robotic arm according to claim 1, wherein the first link is pivotable relative to the second link about a joint, the joint having a curved outer surface, and the surgical robotic arm further includes a second sensor assembly, the second sensor assembly being curved and coupled to the curved outer surface of the joint.

* * * * *